US006221608B1

(12) United States Patent
Middleton et al.

(10) Patent No.: US 6,221,608 B1
(45) Date of Patent: *Apr. 24, 2001

(54) METHODS FOR IDENTIFYING ERYTHROPOIETIN RECEPTOR BINDING PROTEIN

(75) Inventors: Steven A. Middleton, Flemington, NJ (US); Dana Johnson, Upper Black Eddy, PA (US); Frank J. McMahon, Whitehouse Station, NJ (US); Linda S. Mulkahy, Yardley, PA (US); Linda K. Jolliffe, Belle Mead, NJ (US)

(73) Assignee: Ortho Pharmaceutical Corporation, Raritan, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/786,690

(22) Filed: Jan. 22, 1997

(51) Int. Cl.[7] .................................................. G01N 33/566
(52) U.S. Cl. ......................... 435/7.1; 435/7.2; 435/7.21; 436/501; 530/350
(58) Field of Search .................................. 435/7.1, 69.7, 435/7.2, 7.21; 530/350; 436/501

(56) References Cited

U.S. PATENT DOCUMENTS 5,767,078 * 6/1998 Johnson et al. .
5,773,569 * 6/1998 Wrighton et al. ..................... 530/300
5,835,382 * 11/1998 Wilson et al. ........................ 364/496
5,885,574 * 3/1999 Elliott ................................ 424/133.1

* cited by examiner

Primary Examiner—Lorraine Spector
Assistant Examiner—Claire M. Kaufman
(74) Attorney, Agent, or Firm—John W. Wallen, III

(57) ABSTRACT

The extracellular domain of the human erythropoietin receptor (EPO binding protein, EBP) has been expressed and overproduced in *E. coli*. Control of oxygen levels and pH during high density fermentation allows the production of only the protein variant with the native amino terminus. Methods disclosed permit the efficient recovery of purified EBP which quantitatively binds EPO. The active purified protein competes with membrane associated EPO receptor for binding [$^{125}$I]EPO and neutralizes EPO dependent stimulation in a cell based proliferation assay. Further, the radioligand equilibrium binding constant for this interaction has been determined by immobilizing EBP on agarose gel via a free cysteine. The EBP of the present invention has many uses including the structural determination of the protein by NMR or crystallography, in drug design and discovery, and as a therapeutic. A fusion protein of EBP and an immunoglobulin heavy chain was also produced. This protein, termed EBP-Ig, is a preformed dimerization template and is also useful in drug design and discovery methods.

1 Claim, 12 Drawing Sheets

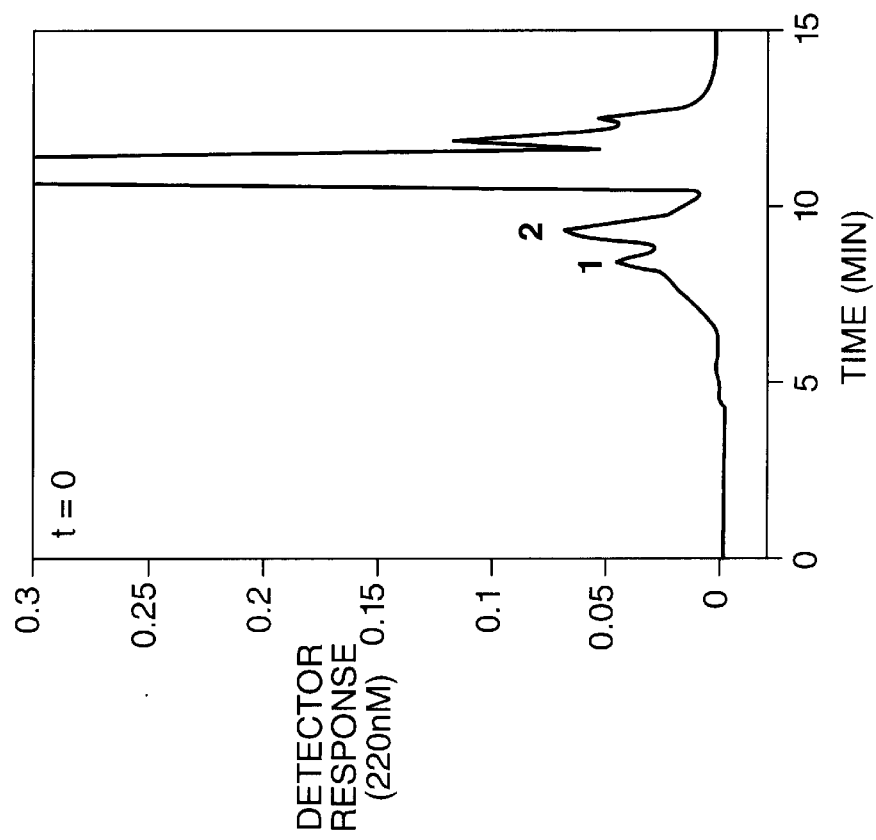

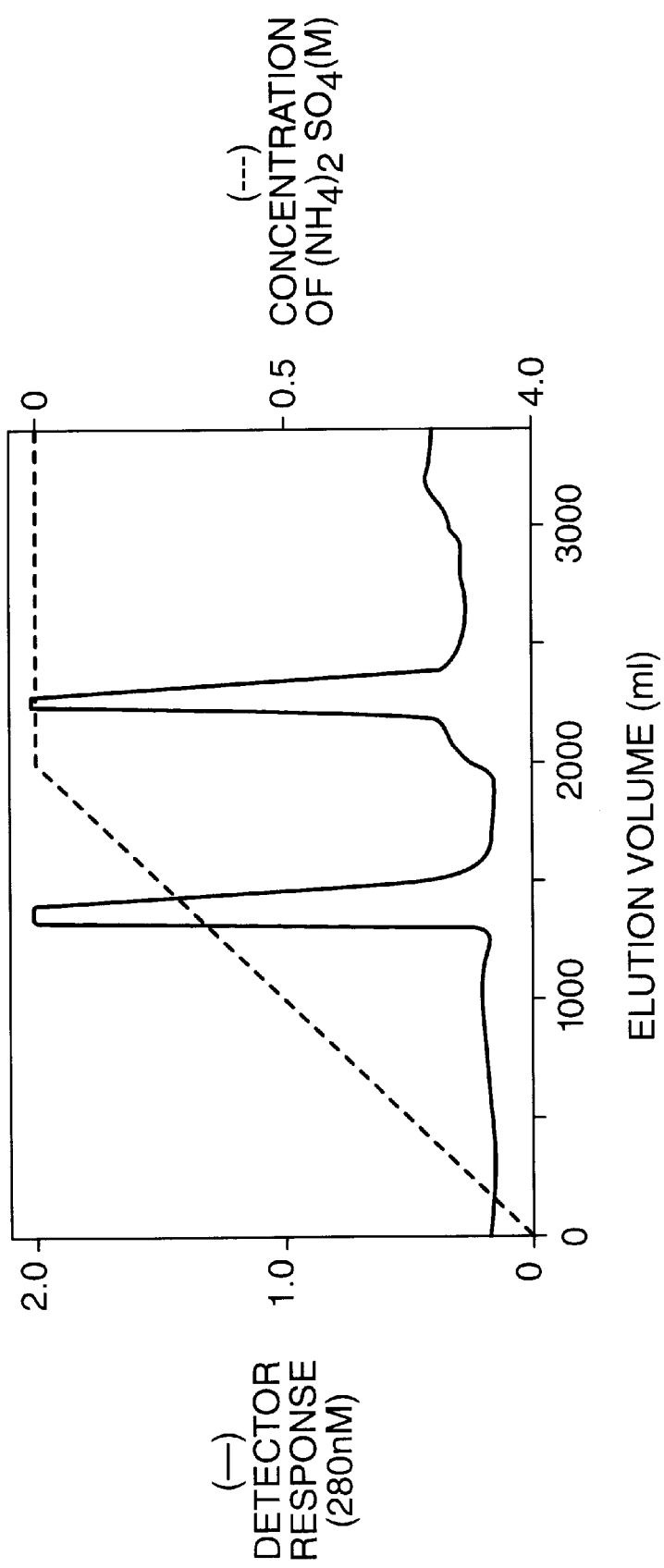

Figure 1:
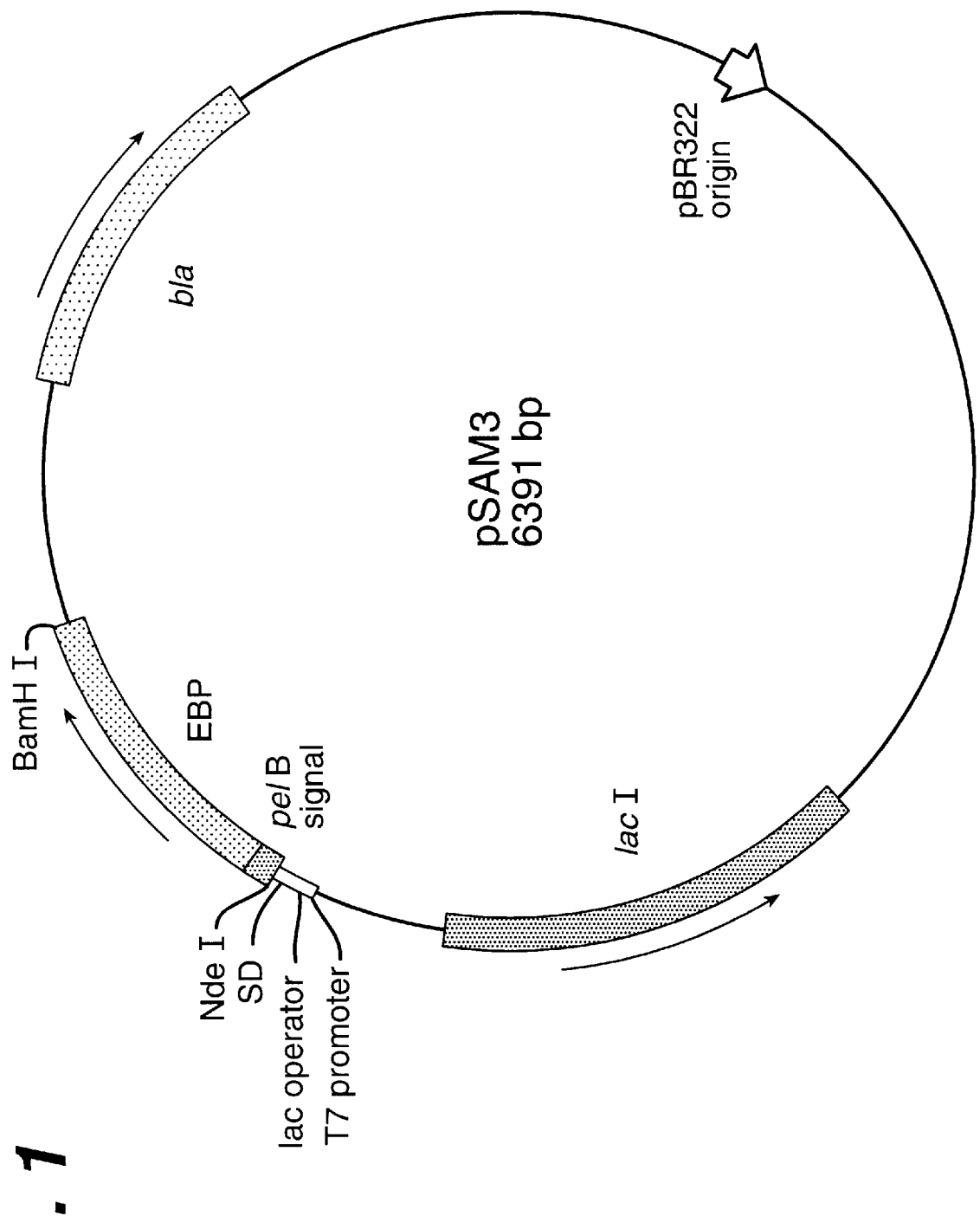

| COMPLEX | EPO (pmol) | EBP (pmol) | RATIO |
|---|---|---|---|
| C#1 | 208 | 178 | 1.17 : 1 |
| C#2 | 340 | 307 | 1.11 : 1 |

METHODS FOR IDENTIFYING ERYTHROPOIETIN RECEPTOR BINDING PROTEIN

BACKGROUND OF THE INVENTION

The hematological process leading to the production and maturation of red blood cells is under the control of erythropoietin (EPO) (reviewed in Krantz, S. B. (1991) Erythropoietin. *Blood* 77, 419–434), a glycoprotein hormone primarily synthesized in the kidney. Commercially available human EPO is produced via recombinant DNA techniques and is known as recombinant human EPO (rhEPO). rhEPO has a molecular mass of approximately 36,000 Daltons, as determined by SDS-PAGE. The molecular mass of the protein backbone is 18,398 Daltons, which indicates that the entire molecule is heavily glycosylated. The carbohydrate residues are important for in in vivo biologic activity.

In contrast to many other growth factors, the specificity of EPO for erythroid cells has lead to its development as a safe and efficacious therapeutic protein. The medical benefits of EPO have been well established in the treatment of anemia associated with chronic renal failure, cancer chemotherapy, and autologous predonation of blood. Due to the chronic nature of EPO therapy, it would be desirable to have an orally administered "second generation" molecule.

An understanding of the structural basis of the interaction of EPO with its receptor will aid in the design of new drugs, such as an oral anemia drug. Traditional methods of drug discovery are being supplemented by rational design approaches that attempt to make use of information about the structural basis of receptor-ligand interactions to develop molecular models. These models, in turn, are used to design molecules with therapeutic potential. The two approaches are complementary and rely on the ability to obtain information about the three-dimensional structure of the therapeutic target. The ability to produce EPO and its receptor and to assess the impact of structural changes on protein function provides a means for testing hypothetical molecular models and contributes to the establishment of a structure activity relationship database for drug design.

The biological effect of EPO appears to be mediated, in part, through interaction with a cell membrane bound receptor which has previously been cloned (Jones, S. S., D'Andrea, A. D., Haines, L. L., and Wong, G. G. (1990), Human erythropoietin receptor: Cloning, expression, and biological characterization, *Blood* 76, 31–35; Noguchi, C. T., Kyung, S. B., Chin, K., Wada, Y., Schecter, A. N. and Hankins, W. D. (1991) Cloning of the human erythropoietin receptor gene, *Blood* 78, 2548–2556; Maouche, L., Tournamile C., Hattab, C., Boffa, G., Carton J.-P. and Chretein, S. (1991) Cloning of the gene encoding the human erythropoietin receptor. *Blood* 78, 2557–2563). Currently there is considerable interest in the physical nature of the association of EPO with the EPO receptor (EPOR) and an emerging technique for the analysis of this type of interaction is the generation of soluble receptors, also termed hormone binding proteins (Langer, J. A. (1990) Soluble ligand-binding fragments of polypeptide receptors in basic and applied research, *Pharmaceutical Technology* 14, 46–66). The process involves the engineering of suitable expression vectors encoding the extracellular domain of the receptor and the subsequent production and purification of the protein. Once obtained in active form, these soluble receptor fragments are useful in numerous assay formats and have improved utility in biophysical studies such as NMR or X-ray crystallography, since they can be employed in conditions free of the detergents required to solubilize membrane bound receptors. Some receptor fragments of this type, including IL-1 and IL-4, function to neutralize the biological effects of the hormone and appear to have therapeutic potential (Maliszewski, C. R. and Fanslow, W. C. (1990) Soluble receptors for IL-1 and IL-4: Biological activity and therapeutic potential, *Trends in Biotech* 8, 324–329).

Previous reports outline the development of systems for the production and purification of human and murine EPO binding protein (EBP) utilizing protein expression in eukaryotic cells and bacteria but with modest yields (Harris, K. W., Mitchell, R. A., and Winkleman, J. C. (1992) Ligand Binding Properties of the Human Erythropoietin Receptor Extracellular Domain Expressed in *E. coli. J. Biol. Chem.* 267, 15205–15209; Yet, M.-G and Jones, S. S. (1993) The Extracytoplasmic Domain of the Erythropoietin Receptor Forms a Monomeric Complex with Erythropoietin. *Blood* 82, 1713–1719; Nagao, M., Masuda, S., Abe, S., Ueda, M. and Sasaki, R. (1992) Production and ligand-binding characteristics of a soluble form of the murine erythropoietin receptor, *Biochem. Biophys. Res. Comm.* 188, 888–897).

The mechanism of EPO receptor activation has been suggested to reside in the dimerization of two EPO receptor molecules which results in subsequent steps of signal transduction [Watowich, S. S., Yohimura, A., Longmore, G. D., Hilton, D. J., Yoshimura, and Lodish, H. F., Homodimerization and constitutive activation of the erythropoietin receptor. Proceedings of the National Academy of Sciences 89, 2140–2144 (1992)]. While the soluble EPO receptor [Johnson, D. L., Middleton, S. A., McMahon, F., Barbone, F., Kroon, D., Tsao, E., Lee, W. H., Mulcahy, L. S. and Jolliffe, L. K., Refolding, Purification and Characterization of Human Erythropoietin Binding Protein Produced in *Escherichia coli*, *Protein Expression and Purification* 7 104–113 (1996)] has advantages related to structure determination and ease of production, it likely does not represent a preformed template for receptor dimerization. In the search for peptides or small molecules which might bind to and activate the EPO receptor such a preformed dimerization template is a highly valuable tool for the discovery, detection, and description of molecules with such activity. Use of receptor-Ig fusion molecules provide such templates and depending upon the assay format provide information on the ability of a given molecule or compound to detect non-productive as well as productive dimerization complexes.

SUMMARY OF THE INVENTION

A new process for the production of highly pure human EPO binding protein (EBP) from fermentations of recombinant host cells is disclosed herein. The described process of the present invention produces a highly pure non-glycosylated EBP which retains the EPO receptor biological property of EPO (ligand) binding. The highly pure EBP of the present invention is also useful in a wide variety of drug discovery techniques, including but not limited to, the design, discovery and production of ligand mimetics, the design, discovery and production of inhibitors of ligand binding, the design, discovery and production of agonists, antagonists and other modulators of ligand binding, and the production of crystal structures which allow the precise characterization of the EBP-ligand interaction site(s). The precise characterization of the EBP-ligand interaction site(s) is also useful for the the design, discovery and production of ligand mimetics, the design, discovery and production of inhibitors of ligand binding, and the design, discovery and production of agonists, antagonists and other modulators of ligand binding.

The EBP is also produced in a recombinant host cell as a fusion protein. An EBP fusion protein comprises the EBP amino acid sequence covalently linked to an additional amino acid sequence. The additional amino acid sequence may provide a means for EBP detection, purification, quantitation, antigenicity or any other desired function. In particular, EBP can be produced as a fusion protein wherein the additional amino acid sequence is an immunoglobulin heavy chain, or a portion thereof. The EBP-Ig of the present invention is a fusion protein of EBP and a portion of the IgG heavy chain that includes the hinge region of the IgG heavy chain molecule. The EBP-Ig is also useful in a wide variety of drug discovery techniques, including but not limited to, the design, discovery and production of ligand mimetics, the design, discovery and production of inhibitors of ligand binding, and the design, discovery and production of agonists, antagonists and other modulators of ligand binding.

The methods for the use of EBP and EBP-Ig in such drug discovery techniques are also disclosed herein.

BRIEF DESCRIPTION OF THE DRAWINGS

FIG. 1. The plasmid vector used for the expression of EBP in *E. coli* is shown.

FIG. 2 Panels 2A and 2B. Reducing (Panel A) and non-reducing (Panel B) 10–20% SDS-PAGE of samples from EBP expression and purification studies are shown.

FIG. 3, Panels 3A, 3B, 3C, and 3D: Demonstration of the detection of the "active" fom of EBP is shown.

FIG. 4, Panels 4A, 4B, 4C, and 4D. Demonstration of EBP purity and activity after purification by HIC and preparative size-exclusion chromatography is shown.

FIG. 5, Panels 5A and 5B. Determination of EPO-EBP complex stoichiometry by C4 reverse phase HPLC is shown.

FIG. 6, Panels 6A and 6B. Equilibrium EPO binding to immobilized EBP and mass spectral analysis is shown.

FIG. 7, Panels 7A and 7B. Competition of EBP for [$^{125}$I]EPO binding to cell associated native EPO receptors, is shown.

FIG. 8, Panels 8A and 8B. Crosslinking of EBP proteins that were dimerized by different peptide ligands is shown by SDS-PAGE under nonreducing conditions (Panel A) and reducing conditions (Panel B).

DETAILED DESCRIPTION OF THE INVENTION

The present invention is drawn to a process for the purification of erythropoietin binding protein (EBP) from microbial fermentations. The present invention is also drawn to the EBP itself, and its use in drug design and discovery techniques. The EBP of the present invention is also useful as a therapeutic since it binds to erythropoietin, making the erythropoietin unavailable for interaction with the cell-associated receptor.

The present invention is also drawn to EBP in the form of a fusion protein. The EBP may be produced in a recombinant host cell as a fusion protein, or may be isolated and purified from recombinant host cells and then chemically reacted with another protein or peptide to form a covalent linkage between the EBP and the protein or peptide. An EBP fusion protein comprises the EBP amino acid sequence covalently linked to an additional amino acid sequence. The additional amino acid sequence may provide a means for EBP detection, purification, quantitation, attachment, antigenicity or any other desired function. In particular, EBP can be produced as a fusion protein wherein the additional amino acid sequence is an immunoglobulin heavy chain, or a portion thereof. The EBP-Ig of the present invention is such a recombinantly produced fusion protein of EBP and a portion of the IgG heavy chain that includes the hinge region of the IgG heavy chain molecule. The EBP-Ig of the present invention is also useful as a therapeutic since it binds to erythropoietin, making the erythropoietin unavailable for interaction with the cell-associated receptor. EBP-Ig is useful in a wide variety of drug discovery techniques, including but not limited to, the design, discovery and production of ligand mimetics, the design, discovery and production of inhibitors of ligand binding, and the design, discovery and production of agonists, antagonists and other modulators of ligand binding.

The term EBP as used herein refers to a form of the EPO receptor that lacks a substantial portion of the membrane anchorage domain and cytoplasmic domain, yet retains the ligand binding domain and the ability to bind eryiropoietin. The term EBP-Ig as used herein refers to a recombinantly produced fusion protein comprising an immunoglobulin heavy chain including the hinge region, and EBP, a form of the EPO receptor that lacks a substantial portion of the membrane anchorage domain and cytoplasmic domain, yet retains the ligand binding domain and the ability to bind erythropoietin. The term EPO mimetic as used herein refers to a compound which binds to the EPO receptor and results in subsequent steps of EPO receptor-mediated signal transduction.

The process of the present invention is suitable for use with microbial fermentations in general. It is readily apparent to those skilled in the art that a wide variety of microbial cells are suitable for use in the process of the present invention, including but not limited to, fungal cells including yeast, and bacterial cells, including *E. coli*. A preferred microbial fermentation is a bacterial fermentation of cells containing the plasmid encoding the EBP or an EBP fusion protein to be isolated and purified. A preferred bacterial fermentation is a fermentation of *E. coli* expressing the EBP or an EBP fusion protein to be isolated and purified. It is readily apparent to those skilled in the art that bacterial fermentations other than *E. coli* fermentations are suitable for use in the present invention. The microbial fermentation may be grown in any liquid medium which is suitable for growth of the bacteria being utilized.

The EBP or EBP fusion protein to be isolated and purified by the process of the present invention can be expressed from any suitable EBP-encoding DNA sequence. The EBP-encoding DNA sequence may be derived from DNA encoding an EPO receptor which itself is derived from a cell line or cell type that expresses an EPO receptor.

The receptor-Ig fusion molecule appears to be particularly well suited for the discovery and description of molecules capable of dimerization (preformed dimerization template protein) of two receptor subunits. A receptor-Ig fusion molecule can be substituted by employing an antibody to an epitope within or linked to the soluble receptor which would allow close association of two soluble receptor molecules. For this purpose, an epitope can be linked to the soluble receptor by chemical coupling or recombinantly by producing a fusion protein. A wide variety of epitopes are suitable for use and include, but are not limited to, polyhistidine epitopes, hemagglutinin, glutathione, and maltose binding protein. The inherent flexibility in these systems would also allow the detection and analysis of multimerizaton complexes. These systems are not limited to the use of erythropoietin receptor and would likely be of similar use in receptors which employ both homogeneous as well as heterogeneous receptor dimerization and multimerization strategies in their signaling cascades. In the case of heterogeneous multimerization, mixtures of two or more soluble receptors or soluble receptor-Ig fusion molecules can be utilized. Other advantages of utilizing receptor-Ig fusion proteins include, but are not limited to, mammalian cell expression and secretion without requiring a protein refolding step, affinity purification of the fusion protein from recombinant host cells, and the known functional and structural properties of immunoglobulin heavy chains which can be exploited.

The EBP-encoding DNA sequence or the EBP-Ig-encoding DNA sequence may be contained on a variety of plasmids which can be high copy number per cell or low copy number per cell. The plasmids can also be of virtually any size. It is readily apparent to those skilled in the art that virtually any plasmid containing the EBP-encoding DNA sequence or the EBP-Ig-encoding DNA sequence that results in the expression of the EBP or EBP-Ig in the recombinant host cells can be used in the process of the present invention.

The cloned EBP-encoding DNA and the EBP-Ig-encoding DNA obtained through the methods described herein may be recombinantly expressed by molecular cloning into an expression vector containing a suitable promoter and other appropriate transcription regulatory elements, and transferred into prokaryotic or eukaryotic host cells to produce recombinant protein. Techniques for such manipulations are fully described in Maniatis, T., Fritsch, E. F., Sambrook, J.; Molecular Cloning: A Laboratory Manual, Second Edition (Cold Spring Harbor Laboratory, Cold Spring Harbor, N.Y., 1989), and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including *E. coli*, bluegreen algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of bacterial expression vectors may be used to express recombinant EBP or EBP-Ig in bacterial cells. Commercially available bacterial expression vectors which may be suitable for recombinant EBP expression include, but are not limited to pET vectors (Novagen), pRSET, pTrcHis, and pTrxFus vectors (Invitrogen), pQE vectors (Qiagen), pFLAG vectors (Eastman Kodak, International Biotechnologies Inc.), pPROEX™-1 (Life Technologies, Inc.), pKK vectors (Clonetech), pP$_L$-Lambda (Pharmacia), and pCal vectors (Stratagene).

A variety of fungal cell expression vectors may be used to express recombinant EBP or EBP-Ig in fungal cells such as yeast. Commerically available fungal cell expression vectors which may be suitable for recombinant EBP or EBP-Ig expression include but are not limited to pYES2 (Invitrogen), Pichia expression vectors (Invitrogen), and pYEUra3 (Clonetech).

A variety of insect cell expression vectors may be used to express recombinant EBP or EBP-Ig in insect cells. Commercially available insect cell expression vectors which may be suitable for recombinant expression of EBP or EBP-Ig include but are not limited to pBlueBacII (Invitrogen), pFastBacl (Life Technologies, Inc.), pBacPAK vectors (Clonetech), and pAc vectors (PHARMINGEN).

A variety of mammalian expression vectors may be used to express recombinant EBP or EBP-Ig in mammalian cells. Commercially available mammalian expression vectors which may be suitable for recombinant EBP or EBP-Ig expression, include but are not limited to, pMAMneo (Clontech), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUC-Tag (ATCC 37460), 1ZD35 (ATCC 37565), and pEe12 (Celltech). Cell lines derived from mammalian species which may be suitable for expression and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, HEK-293 (ATCC CRL1573), and NS0 (ECACC85110503).

DNA encoding EBP or EBP-Ig may be cloned into an expression vector for expression in a recombinant host cell. Recombinant host cells may be prokaryotic or eukaryotic, including but not limited to bacteria such as *E. coli*, fungal cells such as yeast, insect cells including but not limited to drosophila and silkworm derived cell lines, and mammalian cells and cell lines.

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce EBP protein. Identification of EBP expressing host cell clones may be done by several means, including but not limited to immunological reactivity with anti-EBP, and the presence of host cell-associated EBP activity. Likewise, identification of EBP fusion protein expressing host cell clones may be done by several means, including but not limited to immunological reactivity with anti-EBP antibodies, and the presence of host cell-associated EBP activity, as well as immunological reactivity with antibodies specific for the nonEBP portion of the fusion protein, and other host cell-associated activities of the nonEBP portion of the fusion protein.

Because the genetic code is degenerate, more than one codon may be used to encode a particular amino acid, and therefore, the amino acid sequence can be encoded by any of a set of similar DNA oligonucleotides. Only one member of the set will be identical to the EBP sequence but will be capable of hybridizing to EBP DNA even in the presence of DNA oligonucleotides with mismatches under appropriate conditions. Under alternate conditions, the mismatched DNA oligonucleotides may still hybridize to the EBP DNA to permit identification and isolation of EBP-encoding DNA.

It is known that there is a substantial amount of redundancy in the various codons which code for specific amino acids. Therefore, this invention is also directed to those EBP-encoding DNA sequences which contain alternative codons which code for the eventual translation of the identical amino acid. For purposes of this specification, a sequence bearing one or more replaced codons will be defmed as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide. In addition, the alteration of naturally occurring glycosylation sites by site directed mutagenesis using techniques well known in the art may result in the production of a protein which is no longer glycosylated at a particular site. It is readily apparent. to those skilled in the art that an EBP modified in such a manner is an EBP variant within the scope of this invention.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate or a receptor for a ligand.

As used herein, a "functional derivative" of EBP is a protein that possesses a biological activity (either functional or structural) that is substantially similar to the EBP biological activity of EPO binding. The term "functional derivatives" is intended to include the "fragments," "variants," "degenerate variants," "analogs" and "homologues" or to "chemical derivatives" of EBP. The term "fragment" is meant to refer to any polypeptide subset of EBP. The term "variant" is meant to refer to a molecule substantially similar in structure and function to either the entire EBP molecule or to a fragment thereof. A molecule is "substantially similar" to EBP if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire EBP molecule or to a fragment thereof.

As used herein, a "functional derivative" of EBP-Ig is a protein that possesses a biological activity (either functional or structural) that is substantially similar to the EBP-Ig biological activity of EPO binding, and the ability to undergo dimer formation when an EBP ligand is bound. The term "functional derivatives" is intended to include the "fragments," "variants," "degenerate variants," "analogs" and "homologues" or to "chemical derivatives" of EBP-Ig. The term "fragment" is meant to refer to any polypeptide subset of EBP-Ig. The term "variant" is meant to refer to a molecule substantially similar in structure and function to either the entire EBP-Ig molecule or to a fragment thercof. A molecule is "substantially similar" to EBP-Ig if both molecules have substantially similar structures or if both molecules possess similar biological activity. Therefore, if the two molecules possess substantially activity, they are considered to be variants even if the structure of one of the molecules is not found in the other or even if the two amino acid sequences are not identical. The term "analog" refers to a molecule substantially similar in function to either the entire EBP-Ig molecule or to a et thereof.

EBP and EBP-Ig of the present invention are useful in a wide variety of drug discovery techniques, including but not limited to, the design, discovery and production of ligand mimetics, the design, discovery and production of inhibitors of ligand binding, the design, discovery and production of agonists, antagonists and other modulators of ligand binding, and the production of crystal structures which allow the precise characterization of the EBP-ligand interaction site(s). Compounds which are EPO mimetics may be DNA, RNA, peptides, proteins, or non-proteinaceous organic molecules. The present invention is also directed to methods for designing and identifying EPO mimetics and other compounds which modulate binding of EPO to its receptor in vivo. Compounds which modulate these activities may be DNA, RNA, peptides, proteins, or non-proteinaceous organic molecules. Compounds may modulate by increasing or attenuating the expression of DNA or RNA encoding the EPO receptor, or the function of EPO receptor protein. Compounds that modulate the expression of DNA or RNA encoding EPO receptor or the function of EPO receptor protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents.

Methods of the present invention for identifying molecules or compounds which bind to and activate the EPO receptor (EPO mimetics) utilize a preformed dimerization template for the design, discovery, detection, and characterization of molecules with such activity. The term preformed dimerization template as used herein refers to a molecule which exists in solution with two or more potential homologous or heterologous binding domains constrained in sufficiently close physical proximity. Use of receptor-Ig fusion molecules in general provide such templates and provide information on the ability of a given molecule or compound to cause non-productive as well as productive dimerization complexes. Productive receptor dimerization complexes in general have a molecular architecture capable of eliciting signal transduction and subsequent cellular responses, while non-productive receptor dimerization in general results in receptor dimerization lacking specific receptor architecture to promote signal transduction and resulting subsequent cellular responses. Receptor-Ig fusions in general represent the specific ligand binding domains of a given receptor fused to part of an immunoglobulin heavy chain, produced by recombinant techniques, which in turn self associates to form a molecule with two receptor ligand binding domains. EBP-Ig represents one such receptor-Ig fusion and is a preformed dimerization template useful to identify molecules and compounds which can form productive or non-productive EPO receptor dimerization. The molecules and compounds which cause productive EPO receptor dimerization may be EPO mimetics, while molecules and compounds which cause non-productive EPO receptor dimerization may be EPO receptor antagonists. Productive EPO receptor dimerization complexes have a molecular architecture capable of eliciting signal transduction and cellular proliferation while non-productive EPO receptor dimerization results in receptor dimerization lacking specific receptor architecture to promote signal transduction and resulting proliferation.

Pharmaceutically useful compositions containing EBP, modulators of EBP, modulators of EBP-Ig and/or modulators of EPO receptor activity, may be formulated according to known methods such as by the admixture of a pharmaceutically acceptable carrier. Examples of such carriers and methods of formulation may be found in Remington's *Pharmaceutical Sciences*. To form a pharmaceutically acceptable composition suitable for effective administration, such compositions will contain an effective amount of the peptide or protein, DNA, RNA, or modulator.

Following expression of EBP in a recombinant host cell, EBP may be recovered to provide EBP in active form. Microbial cells containing the EBP expression plasmid are harvested from the fermentation medium to provide a cell paste, or slurry. Any conventional means to harvest cells from a liquid medium is suitable, including, but not limited to centrifugation or microfiltration.

The harvested cells are lysed in a suitable lysis buffer. The insoluble proteins are separated from the soluble proteins by conventional methods known in the art, such as centrifugation and microfiltration. The EBP may be present in either or both of the soluble and insoluble protein fractions of the cell lysate.

The EBP produced in the system described below accumulates as an insoluble protein which is then recovered and refolded to obtain an active form of the protein. It is readily apparent to those skilled in the art that the present invention is not limited to insoluble EBP protein, and that soluble protein produced in a recombinant host cell is also suitable for use in the present invention. It is also readily apparent to those skilled in the art that a wide variety of expression vectors and host cells can be used in the present invention, and that the EBP to be expressed may be engineered to contain or lack a signal sequence. In addition, the purification process of the present invention can be used to purify EBP from a mixture of expressed EBP's comprising EBP with and without a signal sequence.

The insoluble protein fraction is collected and solubilized in a suitable solubilization buffer. The solubilized proteins are again separated from the insoluble proteins as described above, and the soluble EBP protein fraction is collected. The solubilized EBP is refolded by incubation for a suitable period of time in a suitable refolding buffer, by conventional methods known in the art. The refolded EBP is then subjected to hydrophobic interaction chromatography using a suitable hydrophobic interaction chromatographic matrix. Examples of suitable hydrophobic interaction chromatographic matrices include, but are not limited to, alkyl or aromatic substituted silica or polymer based resins such as Octyl-Sepharose, Butyl-Sepharose, Phenyl-Sepharose (Pharmacia); Ethyl-, Propyl-, Butyl-, Pentyl-, Hexyl-, Octyl, Decyl-, Dodecyl-, Phenylbutylamine-or Phenyl substituted beaded agarose (Supleco); or Phenyl or Butyl Toyopearl with Phenyl-Toyopearl 650 M being preferred. The proteins are eluted from the hydrophobic interaction column using a suitable elution buffer. The fractions containing active EBP as determined by the methods described herein, are collected. The active EBP is found primarily in the first major protein peak eluted from the column. The column fractions containing the active EBP are pooled and subjected to high-performance size exclusion chromatography (HP-SEC) using a suitable HP-SEC matrix. Suitable HP-SEC matrices include, but are not limited to, porous silica and polymeric gel filtration media including Sephacryl, Sepharose, Superdex and Sephadex Sized Resins; Toyopearl HW, Progel TSK (Supelco) with Bio-Sil SEC-250 (BioRad) or TosoHaas G3000SW being preferred. The fractions from the HP-SEC column that contain EBP activity are pooled and represent extremely pure EBP which binds EPO. This extremely pure EBP is suitable for the uses described herein. It is readily apparent to those skilled in the art that varying the level of EBP purity will provide EBP that may be suitable for the uses disclosed herein.

The initial recovery of EBP from the refold mix may also be accomplished using anion exchange chromatography. Application of a gradient of increasing salt concentration in a suitable buffer results in the elution a two major absorbance peaks of protein with the first major peak containing active EBP. Suitable anion exchange media include, but are not limited to, substituted polymeric or non-porous resins with DEAE or QAE functional modifications including TSK-5w-DEAE, DEAE Sepharose, QAE Sepharose or DEAE Sepharose with DEAE Sepharose FastFlow being preferred. Active EBP recovered in this fashion can be further purified by high-performance size exclusion chromatography (HP-SEC).

The refolding of EBP produced in *E. coli* using the process described herein has identified a long lived but transient protein folding intermediate which ultimately relaxes into the active form of the protein. Active protein purified from 24 hr refolding mixtures appeared identical to that refolded for seven days in ligand binding determinations supporting the conclusion that only a single active form of the protein, independent of refolding duration, was purified by these methods. HP-SEC studies have demonstrated that the intermediate appears to have a greater hydrodynamic volume than the active form of the protein with a retention time corresponding to a protein with a mass approximately twice that of the active form of the protein. This may indicate the participation of a dimeric folding intermediate or an intermediate in which only one of the two predicted domains of the protein is folded resulting in an increased hydrodynamic volume.

The soluble ligand binding domain described herein neutralizes the proliferative properties of EPO as detected by the dose dependent neutralization of an EPO responsive cell line. A molecule with the ability to neutralize EPO, such as the EBP and EBP-Ig of the present invention, may have utility in the treatment of EPO responsive proliferative disorders such as erythroleukemia and polycythemia. EBP can also be used to neutralize EPO in vivo. In addition, the EBP-Ig of the present invention may have improved pharmacological properties resulting from the immunoglobulin heavy chain portion of the molecule.

The process and product of the present invention allows for the production of active, unglycosylated EBP potentially suitable for a variety of uses, including but not limited to, drug design and discovery, as a therapeutic, and for structural investigations by NMR and crystallography. Production of the protein in bacteria permits the facile incorporation of the stable carbon and nitrogen isotopes required for heteronuclear NMR studies and limits the potentially complicating factor of heterogeneity induced by the glycosylation of the protein if produced by mammalian cell culture. In particular, the process for EBP purification of the present invention produces a protein that is suitably pure for crystal propagation, thereby enabling crystallography studies.

To produce EBP-Ig of the present invention, the N-terminal 225 amino acids of the human erythropoietin receptor (EBP) was fused to part of an IgG1 human immunoglobulin heavy chain. The immunoglobulin heavy chain portion retains the hinge region of the heavy chain and produces a EBP-Ig molecule which is a preformed dimerization template. This molecule, referred to as EBP-Ig, is a preformed dimerization template because the immunoglobulin heavy chain portion retains the ability to form covalent disulfide linkage with another heavy chain molecule; in this case two EBP-Ig molecules can become covalently dimerized through disulfide bonding as would two immunoglobulin heavy chain molecules.

The EBP-Ig of the present invention is produced recombinantly through the construction of an expression plasmid containing DNA encoding EBP and DNA encoding the desired portion of an immunoglobulin heavy chain molecule. While the EBP-Ig of the present invention utilizes a heavy chain of an IgGI class of immunoglobulins it is readily apparent to one of ordinary skill in the art that the heavy chain of other classes of immunoglobulins are also suitable for use in the methods of the present invention to produce a protein which is a functional equivalent of EBP-Ig. Other immunoglobulin heavy chain molecules which are suitable for use in the methods of the present invention include, but are not limited to, heavy chains derived from immunoglobulins IgG2, IgG3, IgG4, IgA, IgM, and IgE.

The expression plasmid is transferred into a recombinant host cell for expression and the recombinantly produced biologically active protein is recovered from the host cells. It is readily apparent to those of ordinary skill in the art that a variety of expression plasmids are suitable for the expression of EBP-Ig of the present invention. The preferred expression plasmids for EBP-Ig include, but are not limited to, pSG5, and pEe12.

It is also readily apparent to those of ordinary skill in the art that a variety of host cells are suitable for the expression of the EBP-Ig of the present invention. The preferred host cells are cells which are able to produce biologically active recombinant antibody molecules or portions thereof. The most preferred host cells are mammalian cells, with the most preferred mammalian cells being NS0 cells. NS0 cells are the most preferred cells because of their known ability to produce biologically active recombinant antibody molecules. In addition, NS0 cells do not produce immunoglobulin light chains. It is readily apparent to those skilled in the art that other mammalian cells are suitable for use in the present invention, and include, but are not limited to, NS0, COS and CHO cells.

EBP-Ig produced by the recombinant host cells is purified from the host cells or from the culture medium into which the EBP-Ig was secreted by the host cells. A wide variety of purification processes can be utilized to provide EBP-Ig in sufficient purity for use in the drug discovery methods disclosed herein. Following expression of EBP-Ig in a recombinant host cell, EBP-Ig protein may be recovered to provide EBP-Ig in active form. Several EBP-Ig purification procedures are available and suitable for use and include the purification procedures described herein for EBP. As described above for purification of EBP from recombinant sources, recombinant EBP-Ig may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography. A preferred method is to use affinity chromatography, with Protein G and Protein A/G being most preferred. Protein G or Protein A/G are useful because of the affinity of the immunoglobulin heavy chain portion of the molecule for Protein G and Protein A/G. Protein A is useful but was found to have a lower capacity for EBP-Ig.

In addition, recombinant EBP or EBP-Ig can be separated from other cellular proteins by use of an immunoaffinity column made with monoclonal or polyclonal antibodies specific for EBP or the immunoglobulin heavy chain portion of EBP-Ig.

The following examples are provided to illustrate the present invention without, however, limiting the same thereto.

EXAMPLE 1

Construction of the EBP Bacterial Expression Vector

To direct expression to the periplasmic space, the pelB signal sequence (Lei, S-P., Lin, H-C., Wang, S. S., Callaway, J., and Wilcox, G. (1987), Characterization of the *Erwina carotovora* pelB gene and its product pectate lyase, *J. Bact.* 164, 4379–12; Studier, F. W., Rosenberg, A. H., Dunn, J. J., & Dubendorff, J. W. (1990) Use of T7 RNA polymerase to direct expression of cloned genes, *Methods Enzymol.* 185: 60–89) was fused to the N-terminus of the mature HEPOR (Jones, S. S., D'Andrea, A. D., Haines, L. L., and Wong, G. G. (1990). Human erythropoietin receptor: Cloning, expression, and biological characterization, *Blood* 76, 31–35) by overlap extension PCR (Horton, R. M., Hunt, H. D., Ho, S. N., Pullen, J. K., and Pease, L. R. (1989) Engineering hybrid genes without the use of restriction enzymes: gene splicing by overlap extension, *Gene* 77, 61–68). Two separate DNA fragments, one encoding the pelB signal sequence and one encoding amino acids 1–225 of the extracellular domain of the mature hEPOR were generated by PCR. The terminal 16 nucleotides of the pelB PCR fragment were designed to be identical to the first 16 nucleotides of the EBP PCR fragment so that the two fragments could be used as templates for the overlap extension PCR. The 5' and 3' primers used for the overlap extension PCR were designed to introduce Nde I and BamH I restriction sites, respectively, for subsequent cloning into the bacterial expression plasmid. In addition, the 3' primer introduced a stop codon in place of amino acid 226 of the mature hEPOR. The pelB-EBP PCR fragment was ligated into the Nde I and BamH I sites of the T7 promoter expression vector pET11a (Novagen, Inc., Madison, Wis.) and its sequence confirmed by DNA sequencing. For bacterial expression, the resultant construct, called pSAM3 (FIG. 1), was transformed into *E. coli* strain, BL21(DE3) pLysS, carrying the T7 RNA polymerase on the chromosome under control of the IPTG inducible lac promoter (Studier, F. W., Rosenberg, A. H., Dunn, J. J., & Dubendorff, J. W. (1990) Use of T7 RNA polymerase to direct expression of cloned genes, *Methods Enzymol.* 185: 60–89). EBP is expressed from the T7 promoter under regulation of the lac operator. The genes encoding the lac repressor (lacI) and ampicillin resistance (bla) are also present on the plasmid. Typically, cultures were grown to an $OD_{600}$ of 0.6 to 0.9 in M9ZB medium (Studier, F. W. et al., (1990) supra) containing 100 µg/mL ampicillin and 25 82 g/mL chloramphenicol at which time protein expression was induced with a final concentration of 1 mM IPTG. After a further 2 to 3 hours incubation, cells were harvested and the EBP was isolated and purified as described herein.

Fermentation.

Parental *E. coli* strain BL21(DE3)pLysS (Studier, F. W. et al., (1990) supra) transformed with plasmid pSAM3 (designated SM4) was maintained in M9ZB amp/cap medium [M9ZB amp/cap media per liter: 10 g N-Z-Amine A, 100 ml 10×M9 Minimal Salts (Sigma Chemical Co. St. Louis, Mo.), 5 g NaCl, 1 mM $MgSO_4$, 2% D-glucose, 100 mg ampicillin and 25 mg chloramphenicol] as 8% glycerol stock solutions of an $OD_{600}$=1.0 culture. High density fermentation was carried out in a CF-3000 Fermenter (Chemap Inc., South Plainfield, N.J.) fitted with a 10 liter stirred liter tank. Enriched M9ZB media containing (per liter) 20 g N-Z-amine A, 5 g NaCl, 10 g M9 Minimal Salts, 0.12 g $MgSO_4$, 0.2 g glucose, 100 mg ampicillin and 25 mg chloramphenicol was prepared, filtered through a 0.22 μm Milli-Pak 40 (Millipore Corp.) device and pumped into the fermenter. After equilibration of the medium at 37° C. and 20% dissolved oxygen at pH 6.8 the fermenter was inoculated witH 50 ml of the transformed E. coli glycerol stock (see above). Prior to induction, the pH was maintained via glucose feed (400 g glucose to 1 liter of enriched M9ZB media). When an $OD_{600}$ value of 25.0 was obtained, protein overexpression was induced by the addition of IPTG to a final concentration of 1 mM and the pH reduced to 6.1 by the addition of HCl. The induction phase was allowed to proceed overnight. At harvest the $OD_{600}$ value was 36 and 445 g of cell paste was recovered by centrifugation. The final pH of 6.1 greatly slows the doubling time and the final pH required to limit the rate of cell growth is dependent upon reliable pH control and probe calibration.

The constructed expression vector encodes the initial 225 N-terminal residues of the mature human erythropoietin receptor and includes a pelB signal sequence which, it was anticipated, would direct the expressed protein to the periplasmic space of E. coli to yield soluble, properly folded EBP. Western blot analysis of soluble periplasmic protein preparations and growth media showed low levels of protein present in these preparations after induction. Boiled extracts of cultures analyzed by SDS-PAGE demonstrated two intense protein bands present in induced cultures which were absent in cultures grown under identical conditions except for induction with IPTG. The apparent molecular weight of the smaller species was estimated at 27 kDa while the slower migrating species appeared to be approximately 1.5 kDa larger. Recovery of insoluble protein at the analytical scale led to preparations of protein which appeared to be mainly these two species. N-terminal sequence analysis of this protein, after solubilization, refolding and buffer exchange to PBS, indicated two protein sequences; one which corresponded to the first six amino acids expected for the mature N-terminal sequence of the EPO receptor, and a second that constitutes the first six amino acids of the N-terminal pelB signal sequence. These data, taken together, show that the expression system leads to production of two protein forms, both insoluble and presumably located in inclusion bodies, one which corresponds to EBP having a properly processed amino terminus and one that retains the encoded pelB signal sequence. A signal sequence appears to be required for production of the EBP in this expression system, since a version of plasmid pSAM3 lacking the pelB signal sequence did not express EBP in E. coli strain BL21(DE3)pLysS. Other plasmid constructs or other E. coli strains may be constructed which do not require the presence of a signal sequence for high level production of the EBP. An alternative construct in which the ompT signal sequence was employed has also been observed to generate considerable amounts of overexpressed insoluble EBP.

Figure 2A:
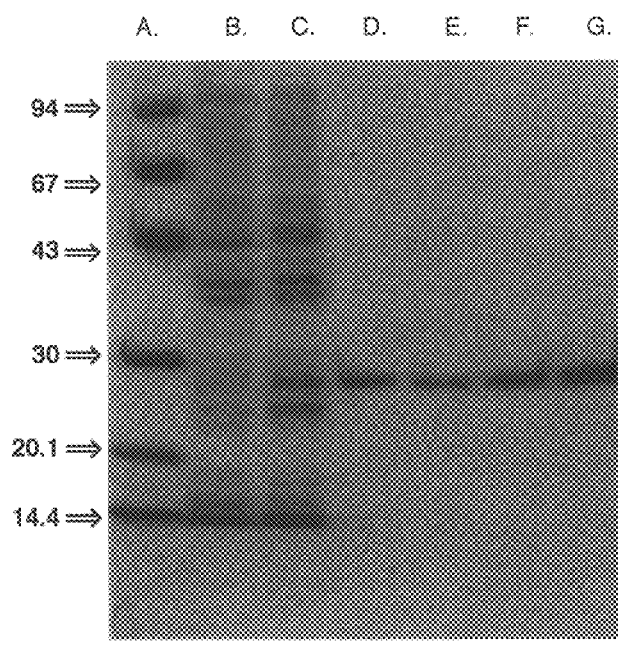
Figure 2B:
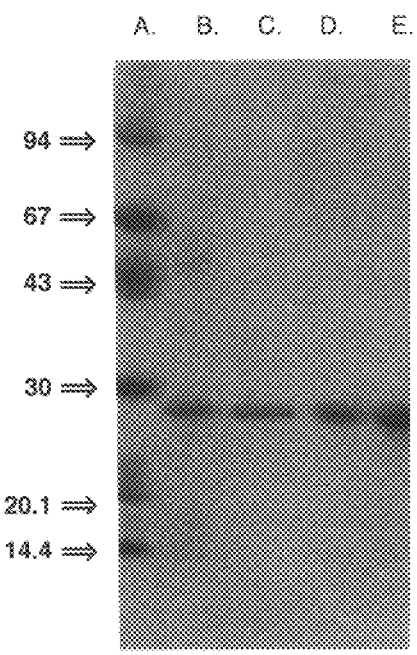

Additional fermentations were performed which varied the distribution of the signal sequence "on" and signal sequence "off" forms of EBP. Initial controlled fermentation studies revealed induced cultures with a greater amount of processed EBP that had a lower final pH. Subsequently an experimental protocol for the production of completely processed EBP was developed. The final fermentation process features a carefully controlled oxygen level and a regulated reduction in the pH of the culture upon induction of protein expression. This results in the expression of a protein species which has an apparent molecular weight of about 27 kDa upon SDS-PAGE analysis (FIG. 2, panel A, lane B versus lane C). Panel A (reduced) samples were as follows: A. Pharmacia LMWM; B. Before induction; C. After induction; D. Refold mix; E. HIC pool; F. HP-SEC pool (2.5 μg); G. HP-SEC pool (5.0 μg). Panel B (non-reduced) samples were as follows: A. Pharmacia LMWM; B. Refold mix; C. HIC pool; D. HP-SEC pool (2.5 μg); E. HP-SEC pool (5.0 μg).

Fermentation under less rigorous control may also be used to obtain EBP which appears as a mixture of "signal sequence on" and "signal sequence processed" material as described above. Insoluble EBP obtained from these fermentations may also be refolded and purified by the methods described herein to yield active protein with a properly processed amino terminus. The refolding and purification result in the separation of the protein form which retains the unprocessed signal sequence.

EXAMPLE 2

Protein Recovery and Protein Refolding

Given the high level expression of insoluble protein we sought conditions for the recovery and refolding of the inclusion bodies to obtain active protein. Conditions were developed based on a number of factors to be considered in the refolding of recombinant proteins (Marston, F. A. O. (1986) The purification of eukaryotic polypeptides synthesized in Escherichia coli. Biochemical Journal 240, 1–12; Light, A. (1985) Protein solubility, protein modifications and protein folding, BioTechniques 3, 298–306; Schein, C. H. (1990) Solubility as a function of protein structure and solvent components, Bio/Technology 8, 308–317). Centrifugation proved adequate for recovery of the inclusion bodies which were found to be optimally solubilized at a concentration of 3.5 M urea. This concentration of urea effectively solubilized >90% of the EBP but left several contaminating proteins in the insoluble fraction. Early experiments on refolding conditions suggested that the process could be followed by high performance-size exclusion chromatography (HP-SEC). The use of HP-SEC was based on the notion that if the pathway of protein refolding proceeds toward either correctly folded active product or various types of protein aggregates, then the use of an analytical technique which discriminates on the basis of molecular volume should predict the efficiency of a refolding protocol alone. Therefore, the protein refolding process was monitored by high performance size exclusion chromatography (HP-SEC) on a Waters 625 HPLC system equipped with a Waters 991 detector. Separations were performed at ambient temperature on a BioSil SEC-250 (7.8×300 mm) (BioRad) column or a G-3000 SWXL (7.8×300 mm) column (Supelco, Bellfonte, Pa.) which provide comparable resolution. The analytical column was equilibrated in 10 mM sodium phosphate, pH 7.2, 150 mM NaCl, at a flow rate of 1 ml/min and was monitored at 220 nm. The active form of the protein was detected by peak shift analysis through the addition of 10 μg of purified recombinant human EPO (1.7 mg/ml, specific activity 120 units/μg) to a 100 μl aliquot of the bulk refold solution followed by HP-SEC analysis. This chromatogram was then compared to the chromatographic resolution of a 100 μl aliquot of bulk refold solution mix performed in the absence of EPO.

Part of the cell paste (74.3 g) from the above controlled fermentation was lysed in 0.3 l of EBP lysis buffer (10 mM TRIS-HCl, pH 7.5, 150 mM NaCl) containing 51 mg of phenylmethylsulfonyl fluoride, 600 mg egg white lysozyme (Calbiochem), 1 mM $MgCl_2$, and 12,500 units of Benzonase (EM Science) and in total termed EBP Lysis Buffer. This mixture was incubated at room temperature for 1.5 hr with occasional agitation. The resulting lysate was centrifuged at 12,000×g for 15 min at 4° C. The supernatant was discarded and pellet was dispersed by application of a one minute burst of sonication after the addition of 0.3 1 of TE buffer (TE buffer: 10 mM TRIS-HCl, pH 7.5, 1 mM EDTA, 3% NP-40[protein grade, Calbiochem]). The resulting suspension was centrifuged for 8000×g for 15 min at 4° C. The supernatant was discarded and the insoluble proteins washed with 0.3 l of water. The pellet was resuspended by sonication (20 sec). Insoluble protein was recovered by centrifugation (12,000×g, 15 min, 4° C.). The wet weight of protein recovered was about 3.5 g after decanting the wash supernatant.

The insoluble protein pellet was resuspended in 9 ml of solubilization buffer per gram of protein (solubilization buffer: 0.1 M TRIS-HCl, pH 8.5, 3.5 M urea, 10 mM lysine, 10 mM dithiothreitol) and was centrifuged at 12,000×g for 15 min at 4° C. Lysine was added to act as a scavenger of amine reactive cyanates possibly present in the urea (Marston, F. A. O. and Hartley, D. L. (1990) Solubilization of protein aggregates, *Methods Enzymol.* 182, 264–276). At this point, the recovered supernatant can be incubated at 4° C. overnight as a convenient stopping point or carried on to the refolding step. The $OD_{280}$ of the solubilized protein was determined against solubilization buffer (21.7 A.U./ml) and 30 ml of the solubilized protein was diluted to 1020 ml in refold buffer (refold buffer: 0.05 M TRIS-HCl, pH 8.5, 3 mM EDTA, 10 mM lysine, 2 mM reduced glutathione, 0.2 mM oxidized glutathione) and stored at 4° C. Final $OD_{280}$ of the refold mix was 0.64.

Figure 3B:
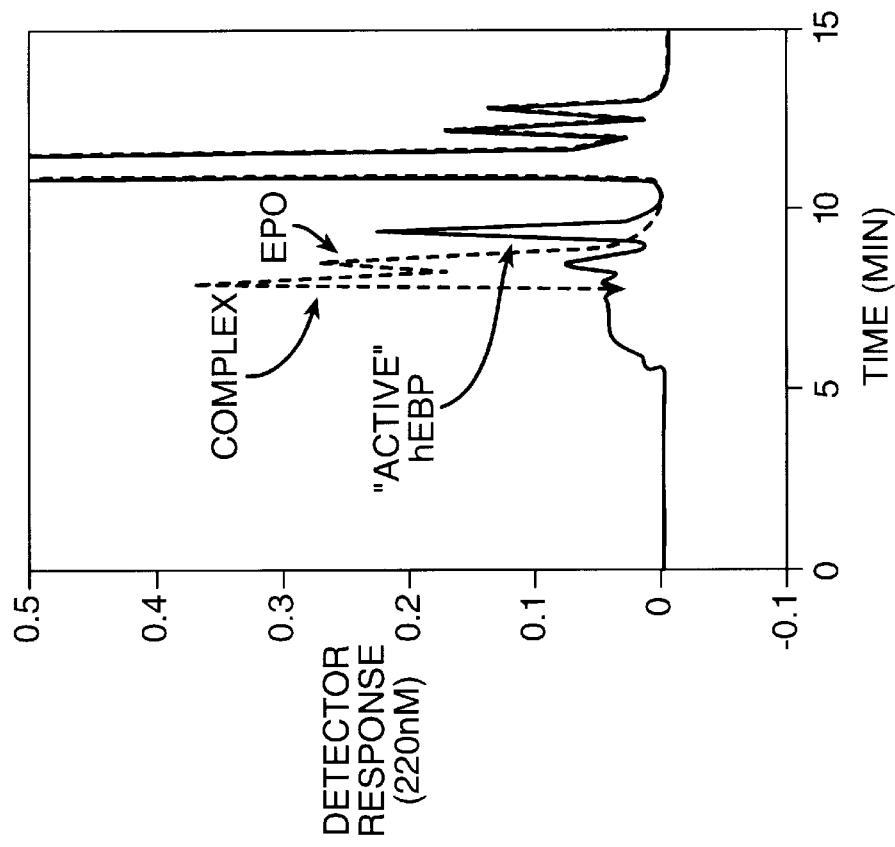
Figure 3A:
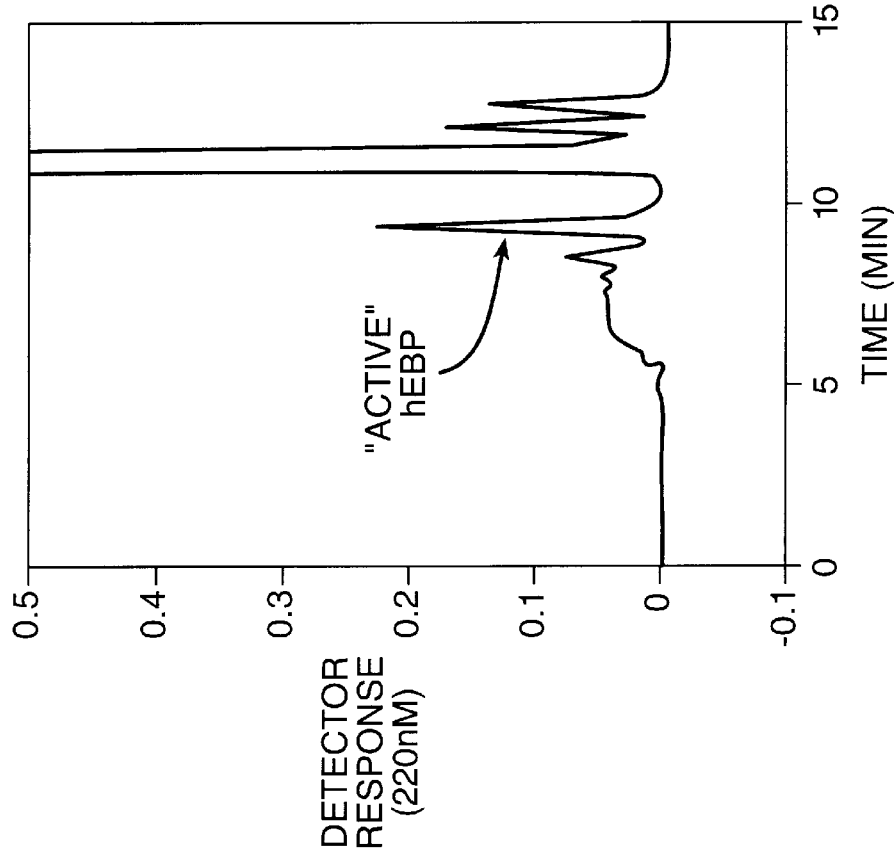

A qualitative estimation of ligand binding activity was possible by performing two HP-SEC experiments with the refold mixture, one with added ligand and one without (FIG. 3). Insoluble EBP was solubilized as described herein and incubated at 4° C. for six days (FIG. 3, Panels A and B). As shown in FIG. 3, Panel A, when the refold mix alone was injected onto an analytical SEC column an absorbance peak was observed at approximately 9.5 min which corresponds to a standard calibrated molecular weight of about 25,000 Daltons. This value is in good agreement with the predicted 24,724 molecular mass of EBP. Upon the addition of 8.5 μg of EPO to the mixture and subsequent chromatographic resolution, an EPO-EBP complex peak was detected at about 8.1 min and an EPO peak at about 8.5 min (FIG. 3, Panel B, overlaid onto the experiment shown in FIG. 3, Panel A). The absorbance peak at about 9.5 min is almost completely depleted demonstrating the presence of an EBP form which can interact with EPO to create a species with a greater apparent solution phase molecular mass. Only the 9.5 min peak appears to interact with EPO indicating a single active species. The peaks eluting after 10 min have calibrated molecular masses of less than 3000 Daltons. FIG. 3, Panel C, shows a significant amount of properly refolded protein is observed immediately after dilution of the 3.5 M urea denaturant solution to 0.1 M urea as evidenced by the peak at the 9.5 min elution time (peak 2). After 24 hrs incubation at 4° C., an increase is observed in both the 9.5 min (Peak 2) active protein form and a species eluting at 8.2 min (Peak 1) as shown in FIG. 3, Panel D. The appearance of these forms appears to be at the expense of higher molecular weight protein forms with retention times of 6–8 min and from insoluble protein in the refolding mix. As shown in FIG. 3, Panel A the 8.2 min protein form gradually decays and the absorbance appears in the active protein peak. These experiments produce clear shifts of a protein of $M_r$=25,000 upon the addition of EPO to an aliquot of the refolding mix (FIG. 3, Panel A and B). Only the $M_r$=25,000 peak appears to shift upon the addition of EPO indicating the presence of a single active species under these analysis conditions.

The HP-SEC study of the refolding mix over time resulted in the observation that a species of $M_r$=52,000 slowly converted into the active $M_r$=25,000 species. (FIG. 3, Panel C, peaks 1 and 2 compared with FIG. 3, Panel A [after 6 days of refolding time]). The refold solution remained slightly cloudy and it was presumed that the insoluble protein giving rise to the opaque solution was slowly entering solution giving rise to additional active and inactive protein species over the initial 24 hours of refolding (FIG. 3, Panels C and D). This metastable species was observed to be long lived and appeared not to be related to a disulfide bonded species, since over the course of the lengthy refolding process non-reducing SDS-PAGE experiments demonstrated no differences with time. This study suggested that continued incubation at 4° C. resulted in the accumulation of additional active product at the expense of the inactive material designated peak #1 (FIG. 3, Panel A) and thus the refolding process was typically carried out for 5–7 days (FIG. 3, Panel C vs. Panel A). Protein with an analytical HP-SEC elution time of 8.2 min (FIG. 3, peak 1) was isolated by preparative HP-SEC and analyzed by SDS-PAGE. Under both reducing and non-reducing conditions the protein appeared to be monomeric. Since this peak ultimately decreases relative to the 9.5 min peak (FIG. 3, peak 2) after several days refolding time (FIG. 3, Panel A) it is suggested that this species might represent a refolding intermediate.

EXAMPLE 3

Protein Purification

Figure 4B:
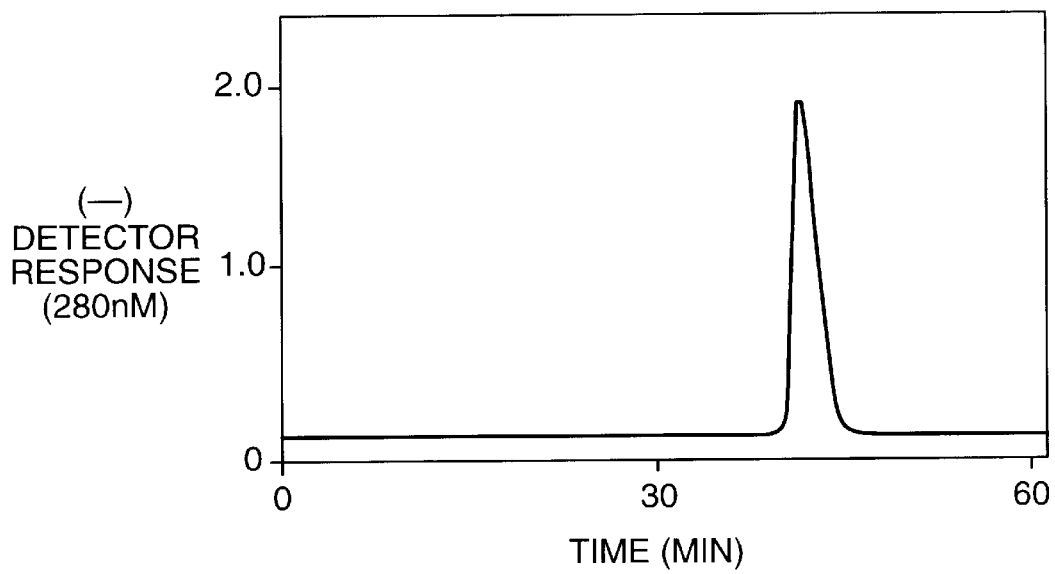

After six days refolding time, the final refold mix was warmed to 37° C. and adjusted to 1 M $(NH_4)_2SO_4$ by the addition of 3.5 M $(NH_4)_2SO_4$ in 20 mM TRIS-HCl, pH 7.5 and additional 20 mM TRIS-HCl, pH 7.5. The final adjusted volume of the 1 M $(NH_4)_2SO_4$ refold mix was 1.5 liter. Analytical HP-SEC analysis of the solution revealed that, in part, the higher molecular weight forms in the refold mix were precipitated from solution. After filtering through a 0.45 μm filter, this solution was applied to a column (5 cm×16 cm) of Phenyl-Toyopearl TSK 650 M (Supelco) at a flow rate of 8 ml/min at room temperature. The column was previously equilibrated with 1 M $(NH_4)_2SO_4$/20 mM TRIS-HCl, pH 7.5 (Buffer A). Upon completion of the column loading, the absorbance (280 nm) of the column effluent was reduced to base line by washing with Buffer A. The protein bound to the column was eluted with a 2000 ml linear gradient of 20 mM TRIS-HCl, pH 7.5 (Buffer B), starting from 100% Buffer A, followed by 1000 ml of Buffer B. A flow rate of 8 ml/min was maintained over the course of the experiment. Fractions of 2 min duration were collected. Two major peaks of absorbance were eluted: one at near 80% Buffer B and another after approximately 200 ml 100% Buffer B FIG. 4A. Analytical HP-SEC of the column fractions (100 μl) indicated that the first absorbance peak contained the active protein and fractions 85–102 were pooled and concentrated by ultrafiltration (Amicon YM-10 membrane). The recovered material was filtered through a 0.45 μm filter before the next chromatography step.

The recovered pool (22 ml, 60 mg protein) was subjected to HP-SEC on a Bio-Sil SEC-250 column (21.5×600 mm, BioRad) equipped with a Bio-Sil precolumn (7.5×21.5 mm) equilibrated with PBS, pH 7.5 at 4 ml/min. Injections of 4.5 ml were made and the entire pool was resolved in five chromatographic experiments. One minute fractions were collected and the active fractions from each run (fractions 40–42) were pooled and concentrated by ultrafiltration in Centriprep 10 devices (Amicon) [FIG. 4B]. The recovered pool (23 ml, 2.04 mg/ml, 46 mg) was analyzed for activity by HP-SEC EPO binding analysis (see below) and for purity by non-reducing and reducing SDS-PAGE analysis (see FIG. 2). SDS-PAGE gels (10–20% gradient SDS-PAG plates, 84×70×1.0 mm, Integrated Separation Systems, Natick, Mass.) were stained with Coomasie Brilliant Blue R-250.

Figure 4C:
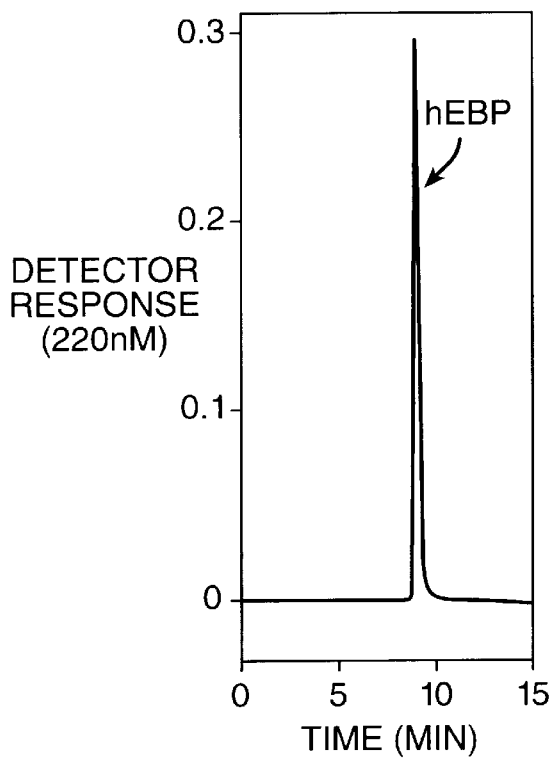
Figure 4D:
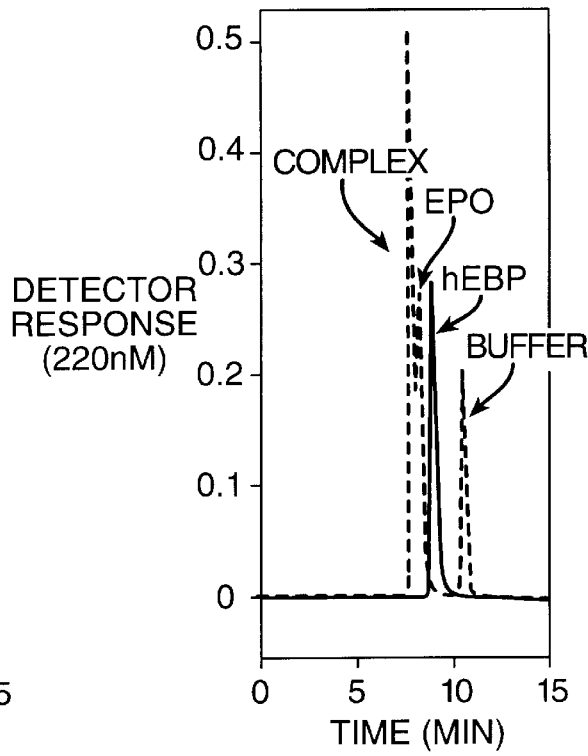

Upon analytical HP-SEC this protein appears as a single species with an elution time of 9.5 min with no trace of high molecular weight aggregates (FIG. 4, Panel C). When mixed with an excess of EPO prior to chromatographic resolution, the EBP observed at 9.5 min is converted to a complex with a retention time of approximately 8.2 min (FIG. 4, Panel D overlaid with experiment shown in FIG. 4, Panel C). If EPO was added at a level below excess one observes the complete depletion of the EPO peak at 8.5 min and the complex peak at 8.2 min remains. A final EBP recovery yield of approximately 0.6 mg active protein per gram of wet cell weight has been observed with 33% overall yield from the refolding stage to apparently homogeneous protein. Table 1 shows the result of the purification of refolded EBP from E. coli.

TABLE 1

| Fraction | Total Protein (mg) | Active EBP[1] (mg) | Yield (%) |
| --- | --- | --- | --- |
| Refold mix | 195 | 138 | 100 |
| HIC | 60 | 58 | 42 |
| SEC | 46 | 46 | 33 |

Note: Starting from 74.3 grams of cells (wet weight). 1-calculated from SEC peak area, based on % of active protein

EXMAPLE 4

Preparation of EPO-EBP Complex and Stoichiometry Determination

Figures 5A, 5B:
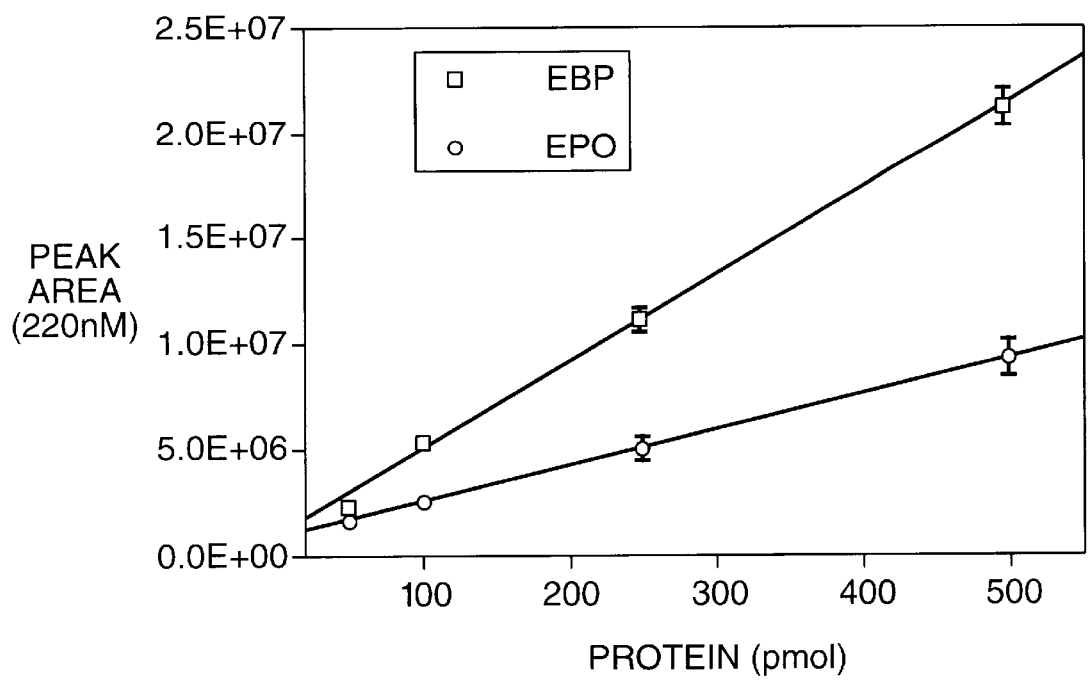

The stoichiometry of EBP and EPO in the binding complex was further examined by the isolation of EPO-EBP complex by HP-SEC, and the estimation of the ratio of protein within this mixture by C-4 reverse phase chromatography as described below. A standard curve of detector response for EPO and EBP (FIG. 5, Panel A) was generated which demonstrated a linear detector response with a low level of repetitive error (1.0 S.D.) over three different analytical runs at each amount of analyte as indicated by the error bars. FIG. 5, Panel B contains the results of the analysis of two different lots of EPO-EBP complex purified by HP-SEC before C-4 analysis. These data, in combination with the HP-SEC data described herein, demonstrate a 1:1 ratio for the EPO-EBP complex.

The complex was obtained as follows. A solution containing 5 mg of EPO and 12 mg of EBP (EBP in excess) was subjected to preparative HP-SEC by the method described above. The first eluting protein peak (EPO-EBP complex) was collected and subjected to analysis by C-4 reversed phase HPLC. Briefly, a 4.6×250 mm column (YMC-PACK, C4-AP, 300 Å) was equilibrated with water/acetonitrile (80%/20%) containing 0.1% trifluoroacetic acid (TFA) and an aliquot of EPO-EBP complex injected at a flow rate of 1 ml/min. After a 5 min wash, a linear gradient of 20–100% acetonitrile containing 0.1% TFA was applied over 20 min and the experiment monitored at 220 nm. Under these conditions, EBP and EPO elute at 14.1 and 15.1 min, respectively, with baseline resolution. A standard curve of each protein was established which demonstrated that detector response was linear over the range of 50 to 500 pmol. The peak area for each protein in the complex was compared to the standard curve to determine the ratio of EPO and EBP in the complex.

EXAMPLE 5

Amino Acid Analysis and N-terminal and Peptide Fragment Amino Acid Sequence Analysis Amino acid analysis of a solution of purified EBP was performed by standard techniques on an 420H hydrolyzer (Applied Biosystems, Foster City, Calif.) and the amino acid content estimated using an internal standard. These data were utilized to calculate a molar extinction coefficient of 57,500 for EBP at 280 nm (2.3 absorbance units/ng) based on the absorbance of the protein solution used for amino acid analysis. This value was subsequently used to estimate EBP concentrations. A calculated extinction coefficient (Gill, S. C. and von Hippel, P. H. (1989) Calculation of protein extinction coefficients from amino acid sequence data. Anal. Biochem. 182, 319–326) of 42,760 was originally employed but was subsequently shown to be inaccurate in binding titration experiments.

The amino terminal sequence of EBP was determined on a 2090E Integrated Micro-Sequencing System (Porton Instruments, Fullerton, Calif.) using standard gas phase Edman degradation chemistry. Repetitive yields were greater than 85%.

For peptide mapping, approximately 50 μg of EBP in PBS was added to 300 μl of 0.05 M TRIS buffer, pH 8.5. To this solution was added 2 μl of 1 mg/ml TPCK-trypsin (Worthington, Freehold, N.J.) in water and the mixture was incubated at 37° C. for 16 hr. The digestion was quenched with 25 μl trifluoroacetic acid and the mixture filtered through a 0.45 μm membrane filter. The digest was analyzed by HPLC on a Dynamax C-18 5 micron 300A column (Rainin Instrument Co., Woburn, Mass.) eluted with a gradient of 0–42% acetonitrile/0.1% TFA over 50 min followed by 42–70% of the same buffer over 10 min at 1.0 ml/min. Fractions of material eluting as 215 nm absorbance peaks were collected and the solvent evaporated in a Speedvac. The peptides were sequenced as above.

To determine the binding capacity of the recovered material and confirm the identity and structural integrity of the protein several additional studies were undertaken. These included N-terminal sequence analysis, TOF mass spectrometry and assay formats designed to determine the ligand binding capacity of EBP. N-terminal sequence analysis demonstrated only the expected N-terminal sequence for ten cycles (see above) to confrmn the identity of the protein. Sequence analysis of several internal tryptic peptides also confirmed the expected linear sequence of the protein and a principle disulfide bonding pattern of 1–2, 3–4.

EXAMPLE 6

Mass Spectrometry

Figure 6A:
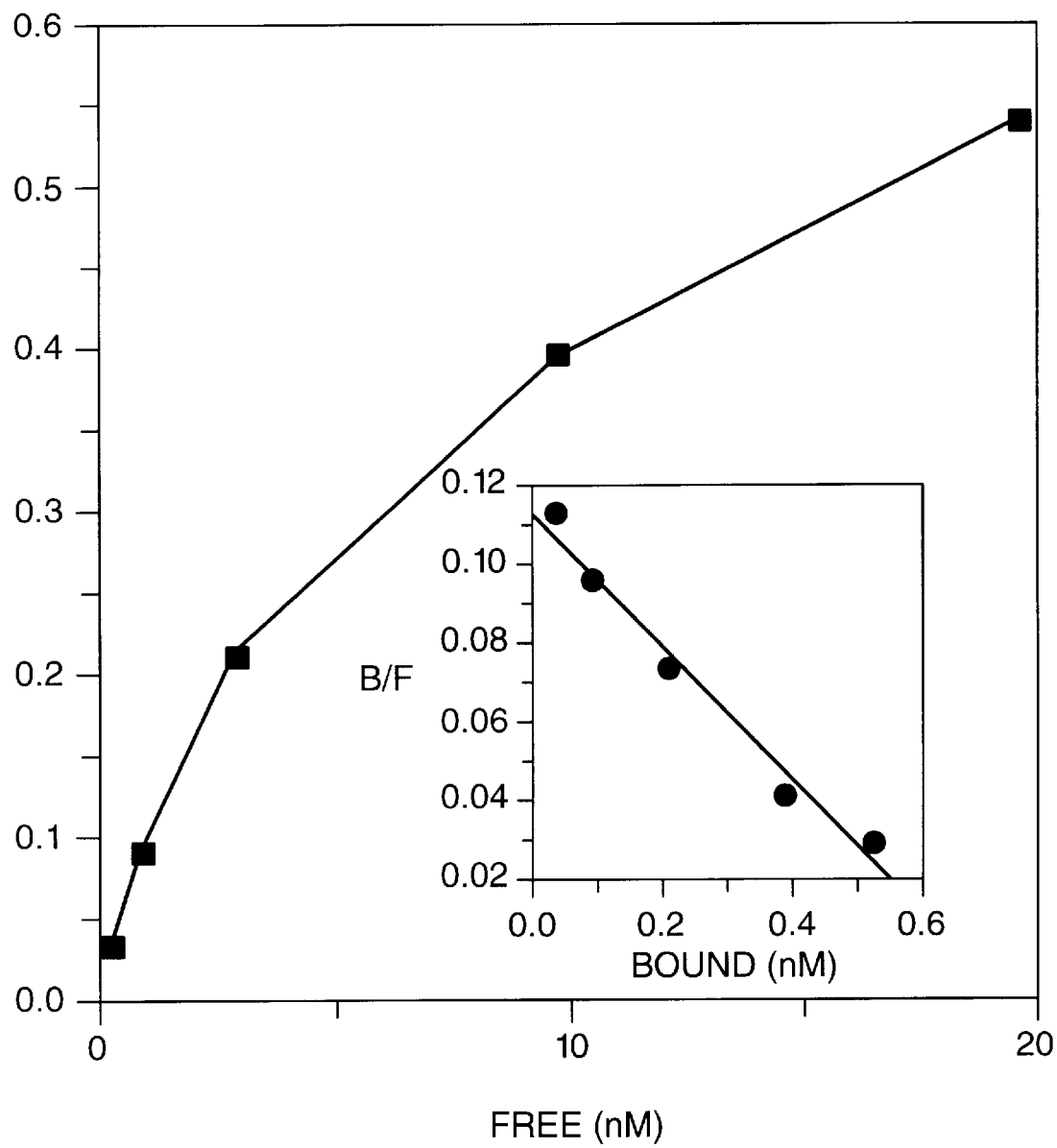
Figure 6B:
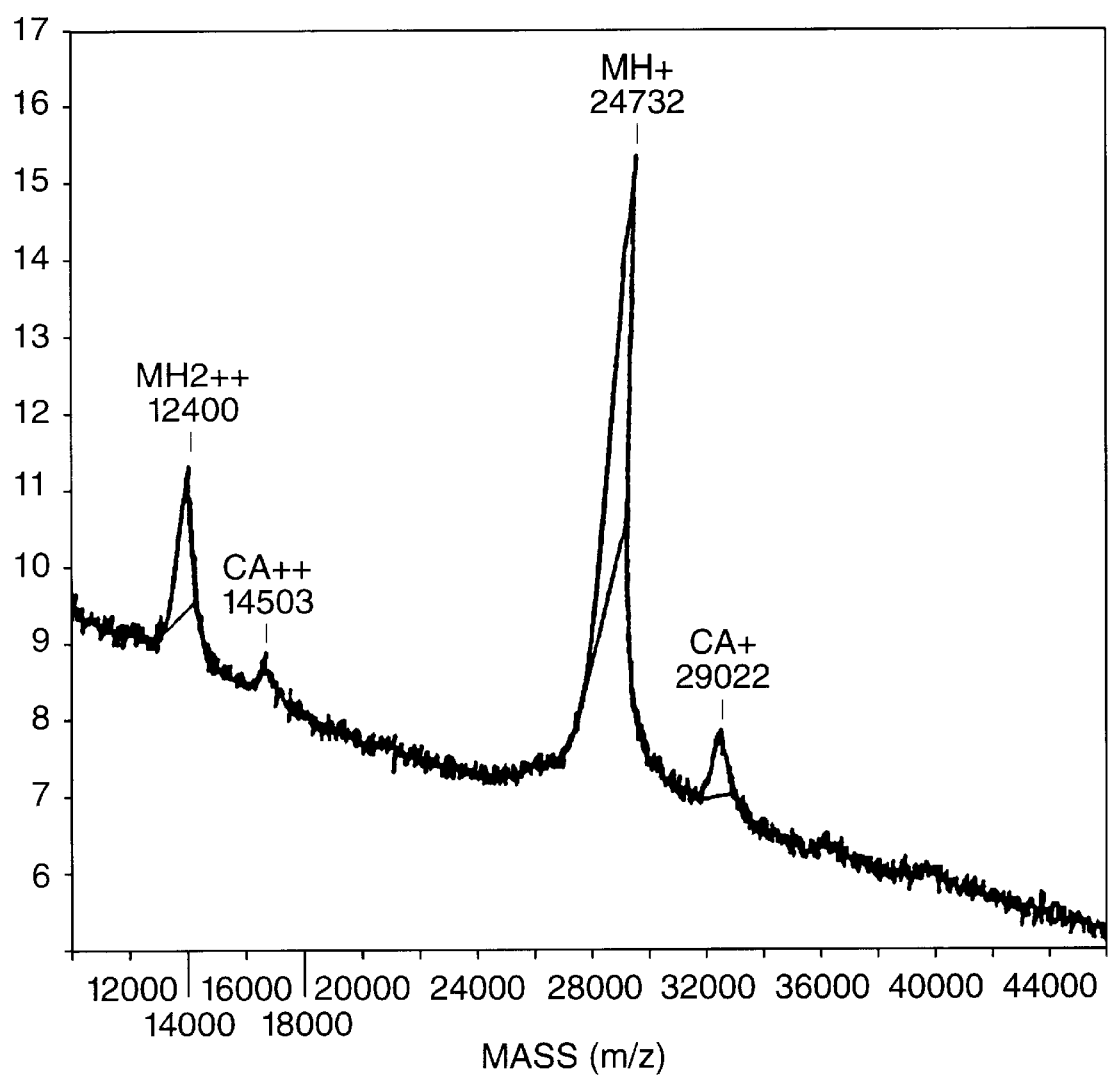

To confirm the mass of the recovered protein, matrix-assisted laser-desorption ionization TOF mass spectrometry was performed on a LaserMAT instrument (Finnigan-MAT, San Jose, Calif.) utilizing a sinapinic acid matrix and an internal bovine carbonic anhydrase mass standard FIG. 6, Panel B demonstrates the MALDI/TOF mass spectrum of EBP showing the molecular ion (MH+) at 24,732 Daltons. The mass centroid of the carbonic anhydrase ion (CA+) was used to calibrate the instrument. Dicharged ions of EBP (MH2++) and carbonic anhydrase(CA++) are also evident in the spectrum. The centroid molecular mass of 24,732 for EBP compares well to the calculated average mass of 24,724 supporting both identity and proper carboxy-terminal truncation of the protein.

EXAMPLE 7

Preparation of EBP Beads and Determination of the Equilibrium Binding Constant (Scatchard Analysis)

EBP as produced by the above method contains one free sulfhydryl group which can be modified without affecting the solution phase binding of ligand. In order to immobilize the EBP for equilibrium binding analysis this observation was extended for the covalent attachment of EBP to agarose beads. The iodoacetyl activation chemistry of Sulfolink beads (Pierce Chemical Co, Rockford, Ill.) is specific for free thiols and assures that the linkage is not easily reversible. EBP-Sulfolink beads were made as follows: Sulfolink gel suspension (10 ml) was mixed with coupling buffer (40 ml: 50 mM TRIS, pH 8.3, 5 mM EDTA) and the gel was allowed to settle. The supernatant was removed and the EBP (0.3–1 mg/ml in coupling buffer) to be bound was added directly to the washed beads. The mixture was rocked gently for 30 minutes at room temperature, and the beads were allowed to settle for 1 hour at room temperature. The supernatant was removed and saved, and the beads were washed twice with 20 ml of coupling buffer. The washes were retained as well. The beads were then treated with 20 ml of 0.05 M cysteine for 30 minutes at room temperature to block unbound sites. Finally, the beads were washed with 50 ml of 1 M NaCl, then with 30 ml of PBS, and resuspended in 20 ml of PBS and stored at 4° C. The amount of EBP which was covalently bound to the beads was determined by comparing the $OD_{280}$ of the original EBP solution to the total $OD_{280}$ recovered in the reaction supernatant and the two 20 ml washes. Typically, 40–60% of the applied EBP remains associated with the beads.

Binding assays were initiated by the addition of EBP beads (50 μl) to individual reaction tubes. Total binding was measured in tubes containing 0.3–30 nM [$^{125}$I]EPO (NEN Research Products, Boston Mass., 100 μCi/μg). For determination of non-specific binding, unlabelled EPO was added at a level of 1000 fold in excess of the corresponding [$_{125}$I]EPO concentration. Each reaction volume was brought to 500 μl with binding buffer (PBS/0.2% BSA). The tubes were incubated for five hours (a time period experimentally determined as adequate for the establishment of equilibrium) at room temperature with gentle rocking. After five hours, each reaction mixture was passed through a 1 ml pipet tip plugged with glass wool. The tubes were washed with 1 ml wash buffer (PBS/5% BSA) and this volume as well as two additional 1 ml washes were passed through the pipet tip and collected for determination of the free EPO concentration. Nonspecific binding was determined from the excess cold EPO experiment at each concentration of radiolabel and subtracted from total binding to calculate specific binding. FIG. 6, Panel A represents the equilibrium binding data and the inset is the linear transformation (Scatchard) of the data set in Panel A and indicates a Kd of 5 nM±2.

EXAMPLE 8

Erythropoietin Receptor Competition Binding Analysis

Figure 7A:
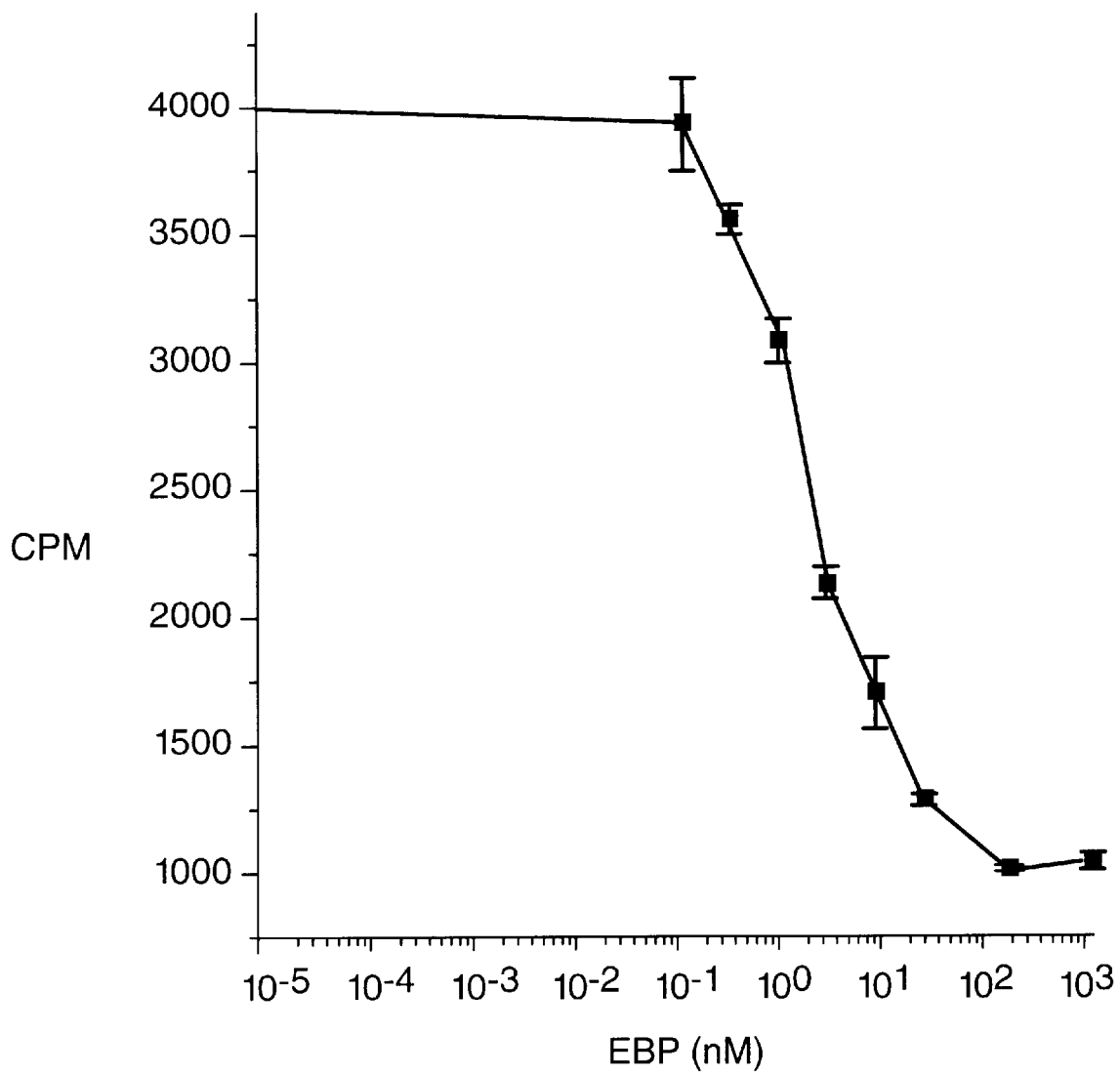
Figure 7B:
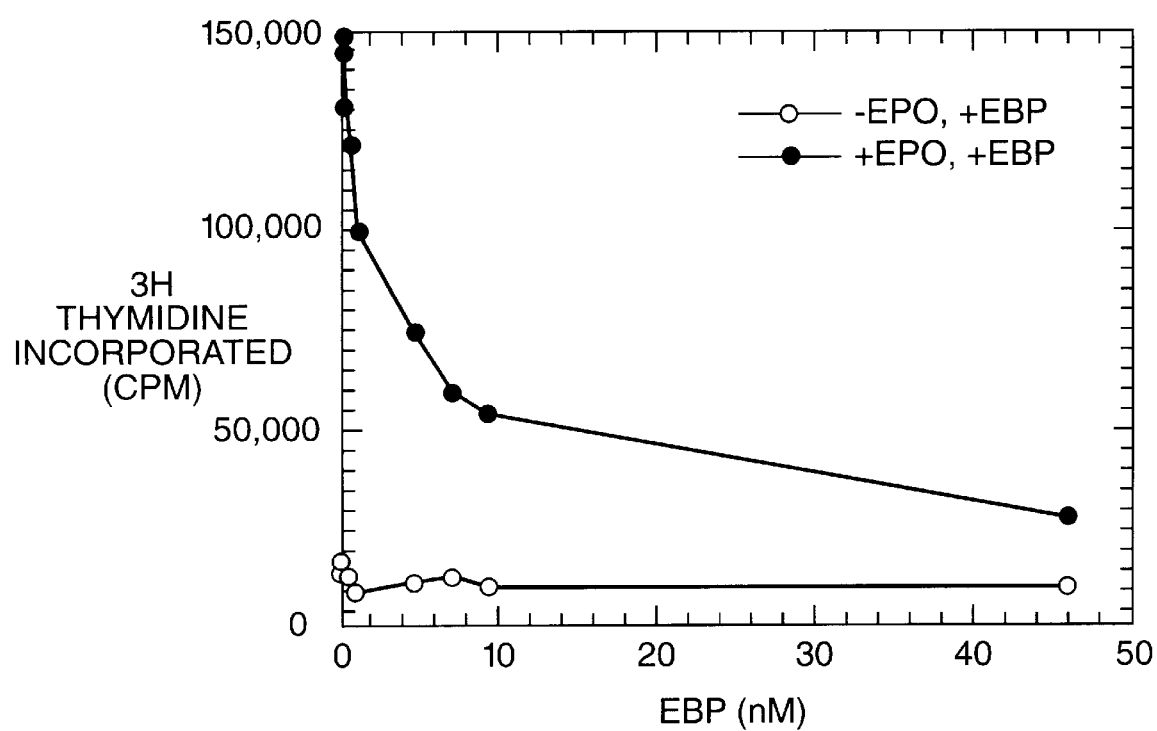

A whole cell-based binding assay was performed by the addition of increasing amounts of purified EBP to a constant amount of [$^{125}$I]EPO and EPOR bearing cells. Nonspecific binding was determined by addition of an excess of EPO (1 μM) and were subtracted prior to data analysis. The estimated $IC_{50}$ and $K_i$ from five assays were determined to be 1.7±1 nM and 0.94±0.5 nM, respectively. Competition of EBP for [$^{125}$I]EPO binding with intact cell surface EPO receptors yielded an $IC_{50}$ of ca. 1.7 nM±1 (FIG. 7, PanelA). Briefly the experiment was performed as follows. TF-1 cells (Kitamura T., Tange T., Teraswa, T., Chiba, S. , Kuwaki, T. Miyagawa, K., Piao, Y.-F., Miyazono,K., Urabe, A. and Takaku, F. (1989) Establishment and characterization of a unique human cell line that proliferates dependently on GM-CSF, IL-3 or erythropoietin. *J. Cell Physiol.* 140, 323–334) were maintained in RPMI 1640, 10% fetal calf serum, 1 % L-glutamine, 1% penicillin, 0.1% streptomycin and 1 unit/ml of IL-3 (Genzyme, Cambridge, Mass.). [$^{125}$I] EPO was obtained from NEN Research Products as described above. Competitive binding studies were performed using a one-stage receptor binding assay method. Briefly, media containing mid-log phase TF-1 cells was centrifuged and the cell pellets resuspended in binding buffer (RPMI 1640, 0.2% BSA, 0.02% sodium azide) at $4 \times 10^7$ cells/ml. To assay binding of EPO to the intact cells, with or without competition from EBP, $4 \times 10^6$ cells, [$^{125}$I] EPO (typically 80 pM) and EBP were mixed and contained within a final volume of 150 μL, in duplicate. Incubations were conducted in 1.5 ml polypropylene tubes at 10° C. overnight. At the end of the incubation period 120 μL aliquots of the binding mixtures were layered onto a 300 μL cushion of 10% sucrose in Sarstedt RIA tubes. Cells were pelleted in a microfuge for 1 min and the tubes were immediately placed in a dry ice bath to quickly freeze the contents. Cells and bound ligand were collected by snipping off the bottom tip of the tube and were transferred to 12×75 mm test tubes for quantification of radioactivity in a gamma counter. Lundon-2 (Lundon Software, Chagrin Falls, Ohio) was employed for data reduction.

EXAMPLE 9

Cell Proliferation Neutralization Assay

Cell line FDC-P1/ER, an EPO-dependent line expressing the murine EPO receptor, was grown and maintained as described previously (Carroll, M. P. ,Spivak, J. L., McMahon, M. , Weich, N., Rapp, U. R. and May, W. S. 1991. Erythropoietin induces Raf-1 activation and Raf-1 is required for erythropoietin-mediated proliferation. *J. Biol. Chem.* 266, 14964–14969). The cells were maintained in RPMI 1640 media (Gibco) containing 10% heat-inactivated fetal calf serum and 10 units/ml of recombinant human EPO. For the inhibition of proliferation assay, FDC-P1/ER cells were grown to stationary phase, centrifuged, washed with RPMI 1640 media (no EPO), and plated in media lacking EPO overnight. Assays were set up in 96-well U-bottom tissue culture plates with each assay point in triplicate. Each well contained $4 \times 10^4$ cells, 0.5 unit/ml EPO, and various amounts of EBP (in media) in a final volume of 0.2 ml. Plates were incubated at 37° C. for ca. 48 hours after which the cells were pulsed with 1 μCi/well of [$^3$H]thymidine (20 Ci/mmol, Dupont-NEN) for 6 hours at 37° C. Cells were harvested onto glass fiber filters using a Tomtec cell harvester. Filters were counted with scintillant using a LKB Betaplate 1205 scintillation counter. The soluble ligand binding domain described herein neutralized the proliferative properties of EPO as detected by the dose dependent neutralization of the proliferative response of EPO in the EPO responsive cell line, FDC-P1/ER. FIG. 7, Panel B shows: Inhibition of EPO dependent cellular proliferation by EBP. The $IC_{50}$ was estimated to be 5 nM±1.

Taken together, the examples shown herein, suggest that the refolded EBP produced in the manner described here is highly active and correlates well to the equilibrium binding constant of EBP produced in CHO cells of 1 nM (Yet, M.-G and Jones, S. S. (1993) The Extracytoplasmic Domain of the Erythropoietin Receptor Forms a Monomeric Complex with Erythropoietin. *Blood* 82, 1713–1719) and the small amount of correctly folded-bacterially expressed EBP-GST fusion protein from an alternative bacterial expression system (Harris, K. W., Mitchell, R. A., and Winkleman, J. C. (1992) Ligand Binding Properties of the Human Erythropoietin Receptor Extracellular Domain Expressed in *E. coli*. *J. Biol.Chem.* 267, 15205–15209) but has advantages which include high purity, it is not a fusion protein, it is non-glycosylated, and it is produced and purified in high yield.

EXAMPLE 10

Peptide Synthesis.

Generically, all of the cyclic EPO mimetic peptides described herein were synthesized using Merrifield solid-phase peptide synthesis methodology on Applied Biosytems Models 430A and 431A Peptide Synthesizers. Protected BOC (t-butoxycarbonyl) amino acid derivatives were coupled as hydroxylbenzotriazole esters after acid deprotection (50% Trifluoroacetic acid/50% dichloromethane) and neutralization (5% diisopropylethylamine/N-methylpyrrolidone) steps. The acid deprotection, neutralization and coupling steps were repeated until the full length peptide-resin was obtained. The completed resin-bound peptide was treated with 50% TFA to yield the free N-terminal peptide-resin. The side-chain protecting groups removed and the peptide cleaved from the resin by treatment with liquid HF-anisole (10% by volume) for 90 minutes at –6° C. The free peptide was then precipitated with cold ethyl ether. Additional ether washes were employed to remove residual scavenger (anisole). The dried peptide-resin was then extracted in 50% HOAc, diluted with water and lyophilized. The cysteines were oxidized by suspending the crude peptide 0.1% TFA/acetonitrile followed by dilution with water to a peptide concentration of 1 mg/ml, which yielded a clear solution (typically 30–50% AcN/water). Solid ammonium bicarbonate was added to the peptide solution until a pH of ca. 8.0 was obtained. Potassium ferricyanide (0.1 M) was added dropwise to the stirred peptide solution until a light yellow solution persisted. This peptide solution was monitored by analytical reverse-phase HPLC for the formation of oxidized product. The cyclic peptides typically eluted after the reduced starting material on a Vydac C18 column. The cyclization reaction time varied from 20 minutes to 18 hours at RT, depending on the particular peptide sequence. Before purification, Bio-Rad AG 2-X8 anion exchange resin (chloride form) was added to the yellow peptide solution to remove the oxidizing agent (iron). The anion exchange resin was removed by filtration and washed with a volume of water equal to the volume of the peptide solution. The combined filtrates were loaded onto a preparative HPLC column (Vydac C18) and the target peptide at 90–95% purity was isolated using a water-acetonitrile gradient with 0.1% TFA. If significant linear peptide was also obtained (typically the reduced peptide eluted closely to the desired cyclic peptide) during chromatography, the oxidation step with potassium ferricyanide was repeated to maximize the overall yield of the reduced target peptide. The fractions collected from the preparative chromatography containing high purity desired peptide were pooled and lyophilized. The final product of each synthesis was characterized by analytical HPLC for purity (usually >95%), ion-spray mass spectroscopy for molecular weight and amino acid analysis for peptide content. All cyclic peptide preparations were negative for free sulfhydryl groups using Ellman's Reagent. The peptides used for the studies disclosed herein are shown in Table 2.

TABLE 2

| EPO mimetic peptides and derivatives | | | |
|---|---|---|---|
| RWJ# | (x) | Peptide sequence* | |
| 61233 | | GGTYSCHFGPLTWVCKPQGG | [SEQ.ID.NO.:1] |
| 61279 | | YSCHFGPLTWVCK | [SEQ.ID.NO.:2] |
| 61177 | | SCHFGPLTWVCK | [SEQ.ID.NO.:3] |
| 62021 | 3,5-dibromo-tyr | GGTXSCHFGPLTWVCKPQGG | [SEQ.ID.NO.:4] |
| 61718 | | GGLYACHMGPMTWVCQPLRG | [SEQ.ID.NO.:5] |
| 61177 | | SCHFGPLTWVCK | |
| 61596 | | GGTYSCHFGPLTWVCKPQ | [SEQ.ID.NO.:6] |

*all peptides are cyclic via an intramolecular disulphide bond and amidated at the -C terminus Competitive binding assays of peptides were performed as described herein. Individual peptides were dissolved in DMSO to prepare a stock solution of 1 mM. All reaction tubes (in duplicate) contained 50 µL of EBP beads, 0.5 nM [125I]EPO (NEN Research Products, Boston, 100 µCi/µg) and 0–500 µM peptide in a total of 500 µL binding buffer (PBS/0.2% BSA). The final concentration of DMSO was adjusted to 2.5% in all peptide assay tubes, a value without detectable effect since an examination of the sensitivity of the assay to DMSO demonstrated that concentrations of up to 25% DMSO (V/V) had no deleterious effect on binding. Non-specific binding was measured in each individual assay by inclusion of tubes containing a large excess of unlabelled EPO (1000 nM). Initial assay points with no added peptide were included in each assay to determine total binding. Binding mixtures were incubated overnight at room temperature with gentle rocking. The beads were then collected using Micro-columns (Isolab, Inc.) and washed with 3 mL of wash buffer (PBS/5% BSA). The columns containing the washed beads were placed in 12×75 mm glass tubes and bound radioactivity levels determined in a gamma counter. The amount of bound [$^{125}$I]EPO was expressed as a percentage of the control (total=100%) binding and plotted versus the peptide concentration after correction for non-specific binding. The IC$_{50}$ was defined as the concentration of the analyte which reduced the binding of [$^{125}$I]EPO to the EBP beads by 50%.

EXAMPLE 11

EPO Dependent Cell Proliferation Assays.

Cell line FDC-P1/hER, an EPO-dependent line expressing the native human EPO receptor was used to determine the EPO mimetic activity of candidate peptides. The cell line exhibits EPO dependent cellular proliferation and the assay was performed as follows. Cells were maintained in RPMI 1640 media (Gibco/BRL) containing 10% heat-inactivated fetal calf serum and 10 units/ml of recombinant human EPO. For the cellular proliferation assay, cells were grown to stationary phase, centrifuged, washed with RPMI 1640 media (no EPO), and plated in EPO minus media for 24 hours.

At 24 hours, the cells were counted, resuspended at 800,000 cells/ml and dispensed at 40,000 cells/well. Stock solutions of the respective peptides (10 mM in DMSO) were prepared and dispensed in triplicate to final concentrations of $1\times10^{-10}$ M through $1\times10^{-5}$ M and adjusted to a final volume of 0.2 ml. Final DMSO concentrations of 0.1% (V/V, maximal) or less were shown to have no cellular toxicity or stimulatory effects. A standard EPO dose response curve was generated with each assay series. After a 42 hours incubation at 37° C. (about 2 cell doublings) 1 µCi/well of [$^3$H] thymidine was added and the incubation continued for 6 hours at which time the cells were harvested and counted to assess [$^3$H] thymidine incorporation as a measure of cell proliferation. Results were expressed as the amount of peptide necessary to yield one half of the maximal activity obtained with recombinant EPO, and are shown in Table 3.

EXAMPLE 12

Dimerization of EBP by EPO mimetic peptides.

Figure 8A:
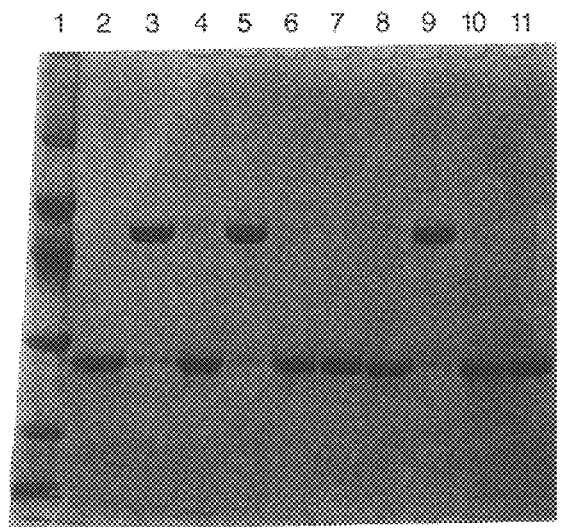
Figure 8B:
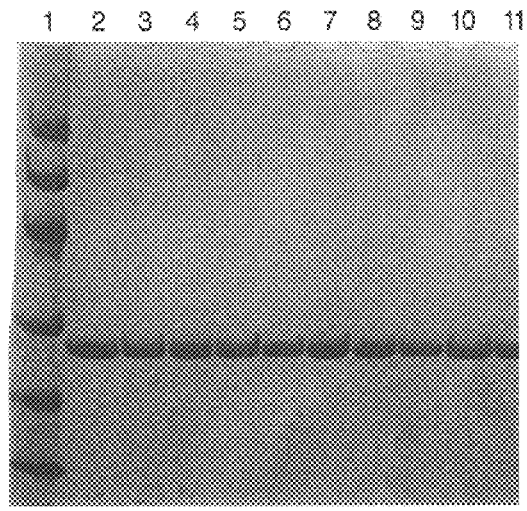

Peptide-mediated receptor dimerization was stabilized for study using the non-water soluble homobifunctional sulfhydryl reactive cross linking reagent DPDPB (1,4-di-[2'-pyridyldithio)propionamido]butane, Pierce Chemical Co., Rockford, Ill.). EBP (22 µM) was incubated in the presence or absence of DPDPB (1.1 mM), 400 µM peptide ligand, 75 µl of PBS, pH 7.5 with all reactions and controls containing a final concentration of 4.4% DMSO and 0.007% TFA. These samples were incubated for 4 hours at room temperature and stored at 4° C. for 12 hours before analysis under reducing and non-reducing conditions by SDS-PAGE (10–20% gradient gels, Integrated Separations Systems, Natick, Mass.). The results are shown in Table 3 as positive, weakly positive, trace or negative based on visual detection of a dimer product, and the SDS-PAGEs are shown in FIG. 8 with the lanes of the SDS-PAGEs containing the samples as follows:

| RWJ Number | lanes | Peptide (µM) | EBP (µM) | DPDPB (mM) |
|---|---|---|---|---|
| 61233 | 3, 4 | 400, 400 | 22, 22 | 1.1, 0 |
| 61279 | 5, 6 | 400, 400 | 22, 22 | 1.1, 0 |

-continued

| RWJ Number | lanes | Peptide (µM) | EBP (µM) | DPDPB (mM) |
|---|---|---|---|---|
| 61177 | 7, 8 | 400, 400 | 22, 22 | 1.1, 0 |
| 61596 | 9, 10 | 400, 400 | 22, 22 | 1.1, 0 | lane 1-molecular weight markers only; lane 11-EBP and DPDPB only.

EXAMPLE 13

Construction of EBP-Ig Expression Vectors

IgG-containing plasmid pSG5209IgG1 [Alegre, M. L., Peterson, L. J., Xu, D., Sattar, H. A., Jeyerajah, D. R., Kowalkowski, K., Thistlethwaite, J. R., Zivin, R. A., Jolliffe, L. K., Bluestone, J. A. A non-activating "humanized" anti-CD3 monoclonal antibody retains immunosuppressive properties in vivo *Transplantation* 57: 1537–1543 (1994)], was digested with restriction enzymes Pst1 and BsiHKA1(BSiHKA1creates compatable DNA ends with Pst1) to isolate the IgG1 constant region DNA fragment. The isolated IgG1 fragment was subcloned into plasmid pSG5p35sig, which had been digested with restriction enzyme Pst1. Plasmid pSG5p35sig contains the B72.3 signal sequence [Whittle, N., Adair, J., Lloyd, C., Jenkins, L., Devine, J., Schlom, J., Raubitschek, A., Colcher, D., Bodmer, M. Expression in COS cells of a mouse/human chimaeric B72.3 antibody *Prot. Engin.* 1: 499 (1987)]. The bacterial clones containing the IgG1 constant region in the correct orientation were verified by restriction enzyme digestion analysis.

The EBP DNA was amplified using the polymerase chain reaction (PCR) and oligonucleotide primers specific for the termini: 5' GCATCTGCAGCG CCCCCGCCGAATCTTC-CGGAC [SEQ.ID.NO.:7] and 3' TCACTCTGCAGAGTC-CAGGTC GCTAGGCGTCAG [SEQ.ID.NO.:8]. These primers had a Pst1restriction enzyme site engineered onto the 5' end to facilitate cloning into the pSG5p35sig plasmid. The EBP DNA was purified and ligated into plasmid pSG5p35sig containing the constant region from IgG1. Following transformation into bacteria, EBP-containing clones were identified using PCR and plasmid DNA was purified from selected clones. The DNA sequence was verified using an automated DNA sequencer (Applied Biosystems Inc.).

The EBP-Ig fusion construct in pSG5p35 (designated EBP-Ig wild type) was modified by site directed mutagenesis to produce a second construct that contained three mutated amino acids in the hinge region of the Ig. The amino acid sequence of the EBP/Ig junction is Ser-Ala-Glu-Pro-Lys-Ser-Cys-Asp-Lys [SEQ.ID.NO.:9] reading from the 5' portion of the Ig hinge in the wild type construct. This amino acid sequence was mutated to Ser-Ala-Glu-Pro-Ser-Ser-Ser-Asp-Ser [SEQ.ID.NO.:10] and the resulting construct was designated EBP-Ig 3S.

The pSG5p35sigEBP-Ig constructs allow transient expression in mammalian cells. In order to establish stable cells lines tranformed with either wild type or 3S EBP-Ig, the EBP-Ig fusion was subcloned from the pSGSp35sig plasmid construct and ligated into the plasmid pEE12 [Celltech Limited, Berkshire, UK].

Establishment of NS0 Expression Cell Lines

Stably transformed cell lines expressing the EBP-Ig fusion protein were obtained by transfecting the EBP-human IgG1-pEE12 constructs (3S mutant and wild-type) into NS0 mouse myeloma cells. Selection of transfected cells was carried out using the dominant selectable marker gene, glutamine synthetase (GS).

The NS0 mouse myeloma cell line (Celltech, Ltd.) was a subclone derived from NS-1 and does not express intracellular light chains. These cells were cultured in DMEM medium with added glutamine and 10% FBS. In preparation for transfection, the cells were harvested in mid-log phase of growth and washed with PBS. The final cell pellet was resuspended in 3.6 ml of PBS to a final concentration of $2.5 \times 10^7$ cells/ml. Cells were maintained on ice during the entire procedure.

The DNA to be transfected (EBP-IgG-3S, EBP-IgG-wild-type) was converted to linear form by restriction digest prior to transfection. The DNA and NS0 cells were combined in a 0.4 cm BioRad Gene Pulser cuvette as follows in the indicated order: 48 ul (30 ug) EBP-IgG-3S DNA, 312 ul dd H2O, 40 ul 10×PBS, and 400 ul NS0 cells or 68 ul (45 ug) EBP-IgG-wild-type DNA, 292 ul dd water, 40 ul 10×PBS, and 400 ul NS0 cells. A control cuvette contained 400 ul 1×PBS and 400 ul NS0 cells.

Transfection was performed by electroporation as follows: Cells and DNA in 1×PBS buffer were exposed to a brief, high voltage pulse to induce formation of transient micropores within the cell membrane to facilitate DNA transfer. The suspension of NS0 cells and DNA was gently mixed and incubated on ice for 5 minutes. The cuvettes were placed in a BioRad Gene Pulser and given 2 consecutive electrical pulses at settings of 3 uF (capacitance) and 1.5V (voltage). Following electroporation, the cuvettes were returned to the ice for 5 minutes. The suspension was then diluted in prewarmed growth medium and distibuted into (7) 96-well plates for each DNA construct. Control plates containing cells electroporated without DNA were also prepared at the same time to measure the presence of spontaneous mutants. Plates were placed in a 37° C. incubator with 5% $CO_2$.

Glutamine synthetase, encoded by the GS gene, is an enzyme which converts glutamate to glutamine. NS0 cells require glutamine for growth due to inadequate levels of endogenous GS gene expression. In the DNA constructs, this gene is located on the pEe12 vector. Transfected cells which incorporate the GS gene become glutamine-independent. Cells not integrating the GS gene into their genome would remain glutamine-dependent and not survive in glutamine-free medium. Approximately 18 hours post electroporation, all plates were fed with glutamine-free selection medium and incubated until viable colonies appeared.

Approximately 3 weeks post transfection, distinct macroscopic colonies were observed. These were screened for expression of the EBP-Ig fusion protein using an ELISA assay. In this assay, microtiter plates were coated with goat anti-human Fc polyclonal antibody. Tissue culture samples were added to the wells and incubated to allow a complex to form. Monoclonal anti-human EBP antibody was then added and incubated, followed by the addition of goat anti-mouse IgG antibody conjugated to horseradish peroxidase. After another incubation period, o-phenylenediamine (OPD) substrate was added for detection. Test samples positive for EBP-Ig expression show a yellow to orange color change. The intensity of the color is proportional to the amount of specific protein present. Tissue culture supematants from wells containing colonies were screened at 1:10 or 1:40 dilutions. Wells with cells producing the largest amount of immunoglobulin were selected and expanded for further analysis.

In order to further select for cells producing significant EBP-Ig, protein production was quantitated after a 96 hour growth period. Tissue culture flasks were seeded with $2 \times 10^5$ cells/ml in 10 ml of selection medium and incubated at 37° C., 5% $CO_2$ for 96 hours. At the end of that time period, an aliquot was taken to determine cell concentration and titer. Evaluation of production was calculated as ug/ml per 96 hours. Two high producers, 3A5(3S mutant) and 4H3 (wild-type), gave values of 29 ug/ml and 23 ug/ml respectively. These 2 lines were expanded, frozen and subsequently subcloned by limiting dilution. Approximately 3 weeks after subcloning, single cell clones were screened by ELISA at a 1:100 dilution. One high producing subclone was selected for each line, evaluated for 96 hour production and frozen. ELISA values were 281 ug/ml/96 hours (3A5G1) and 123 ug/ul 96 hours (4H3H12).

For large-scale production, cells from subclones 3A5G1 (3S mutant) and 4H3H12 (wild-type) were expanded into 850 $cm^2$ Coming roller bottles. For 3A5G1, a total of 22 roller bottles were inoculated with $4 \times 10^7$ cells per bottle in CDR-3 serum-free medium. For cell line 4H3H12, a total of 23 bottles were inoculated with $4 \times 10^7$ cells per bottle in CDR-3 serum-free medium. Bottles were gassed with 10% $CO_2$ and incubated at 37° C. for 14 days. The conditioned medium was harvested, centrifuged and sterile filtered in preparation for purification.

EXAMPLE 14

Purification of EBP-Ig

Conditioned media from EBP-Ig (3S mutant) producing NS0 cells (4.5 liter) was diluted 1:2 with PBS and pumped onto a 100 ml column of Protein G (Pharmacia), previously equilibrated with PBS, in 1.5 liter batches. After loading, the column was washed with PBS until the $OD_{280}$ at the column outlet returned to baseline. Bound protein was eluted in batch mode using 20 mM sodium citrate, pH 3.0, and the protein containing fractions pooled. The pH of these fractions was adjusted to 7.0 by the addition of 1 M TRIS base. This procedure was repeated three times to process the entire volume of conditioned media and the material from the three experiments pooled. Total yield from the 4.5 liter starting material was about 440 mg (about 0.1 mg/ml). Protein G was used as the affinity media because preliminary experiments had demonstrated low capacity of Protein A for EBP-Ig.

EXAMPLE 15

EBP-Ig Flash Plate EPO Radioligand Binding Assay

EBP-Ig fusion protein was purified by affinity chromatography from the conditioned media of NS0 cells engineered to express a recombinant gene construct which functionally joined the N-terminal 225 amino acids of the human EPO receptor and an Ig heavy chain as described herein. The interaction of biotin and strepavidin is frequently employed to capture and effectively immobilize reagents useful in assay protocols and has been employed here as a simple method to capture and immobilize EBP-Ig. EBP-Ig is initially randomly modified with an amine reactive derivative of biotin to produce biotinylated-EBP-Ig. Use of strepavidin coated plates allows the capture of the biotinylated EBP-Ig on the surface of a scintillant impregnated coated well (Flash plates, NEN-DuPont). Upon binding of $[^{125}I]$EPO to the ligand binding domain, specific distance requirements are satisfied and the scintillant is induced to emit light in response to the energy emitted by the radioligand. Unbound radioligand does not produce a measurable signal because the energy from the radioactive decay is too distant from the scintillant. The amount of light produced was quantified to estimate the amount of ligand binding. The specific assay format was suitable for the multi-well plate capacity of a Packard TopCount Microplate Scintillation counter. Compounds, peptides or proteins which were capable of reducing the amount of detected signal through competitive binding with the radioligand were identified.

Biotinylated EBP-Ig (3S mutant) was prepared as follows. EBP-Ig (3 ml, $OD_{280}$ 2.9) was exchanged into 50 mM sodium bicarbonate, pH 8.5 using a Centriprep 10 ultrafiltration device. The final volume of the exchanged protein was 1.2 ml ($OD_{280}$2.6, representing about 2 mg total protein). 10 µl of a 4 mg/ml solution of NHS-LC-Biotin (Pierce) was added and the reaction mixture placed on ice in the dark for two hours. Unreacted biotin was removed by exchange of the reaction buffer into PBS in a Centriprep 10 device and the protein reagent aliquoted and stored at −700° C.

Each individual binding well (200 µl) contained final concentrations of 1 µg/ml biotinylated EBP-Ig, 0.5 nM [$^{125}$I]EPO (NEN Research Products, Boston, 100 µCi/µg) and 0–500 µM test peptide (from a 10 mM stock in 100% DMSO). All wells were adjusted to a final DMSO concentration of 5%. All assay points were performed in triplicate and with each experiment a standard curve for unlabelled EPO was performed at final concentration of 2000, 62, 15, 8, 4, and 0 nM. After all additions were made, the plate was covered with an adhesive top seal and placed in the dark at room temperature overnight. The next day all liquid was aspirated from the wells to limit analyte dependent quench of the signal, and the plates were counted on a Packard TOPCOUNT Microplate Scintillation Counter. Non-specific binding (NSB) was calculated as the mean CPM of the 2000 nM EPO wells and total binding (TB) as the mean of the wells with no added unlabelled EPO. Corrected total binding (CTB) was calculated as: TB−NSB=CTB. The concentration of test peptide which reduced CTB to 50% was reported as the $IC_{50}$. Typically the $IC_{50}$ value for unlabelled EPO was ca. 2–7 nM. The results are shown in Table 3.

EXAMPLE 16
Fluorescence Polarization Mimetic Peptide Ligand Binding Assay

Fluorescence polarization (FP) is a useful technique capable of providing information on changes in molecular volume which occur upon the association or dissociation of two molecules. If a smaller molecule with an affinity for a significantly larger one is fluorescently labeled, then the observed fluorescence polarization value increases significantly upon binding and is quantifiable. Conversely, if a non-fluorescent competitor molecule is added to this complex then a decrease in the fluorescence polarization value can be anticipated [Checovich, W. J., Bolger, R. E. & Burke, T. Fluorescence polarization-a new tool for cell and molecular biology, Nature 375, 254–256 (1995)]. RWJ 61718 was labeled with a fluorescein reporter group by treating 10 mg of peptide solubilized in 3 ml of PBS with 17.9 mg of fluorescein isothiocyanate dissolved in 1 ml DMSO (added in 100 µl aliquots). RWJ 61718 contained a single amine (N-terminus) and 1:1 label incorporation was expected. This mixture was placed on ice and the solution cleared by the addition of 1.0 ml of DMSO. Following a 34 hour incubation at 4° C., fluorescein labeled RWJ 61718 was isolated by reverse phase HPLC. The entire reaction mixture was diluted 1:2 with 0.1% trifluoroacetic acid (TFA; mobile phase A), pumped onto a C-18 reversed phase preparative column (Vydac #218tp54) at 8 ml/min and eluted with a 90 minute linear gradient of 0–100% mobile phase B (acetonitrile containing 0.7% TFA). Fractions containing fluorescent products (excitation wavelength 488 nm, emission wavelength 530 nm) at 530 nm were collected and lyophilized. A highly fluorescent peak eluting at near 60 minutes (ca 60% mobile phase B) was determined to be the desired product by monitoring FP changes in the presence of EBP-Ig.

A competitive FP assay using fluorescein labeled RWJ 61718 as the receptor ligand was established as follows using a Fluorescence Polarization Microtiter System (Jolley Consulting). Test peptides at variable concentrations and EBP-Ig (3S mutant, 0.025 mg/ml) were incubated for 1 hour at room temperature in 90 µl PBS and dispensed into a Dynatech Microfluor plate 96 well plate. Fluorescein-RWJ 61718 was added to each well (10 µl in 0.1% TFA) to a final concentration of 2.5 µM followed by an additional 1 hr incubation at room temperate in the dark. Values for milli-Polarization (mP) were obtained at an instrument voltage setting of 8.0. Baseline peptide values were determined from wells which contained only labeled peptide and PBS. Total mP readings were determined in test wells which contained labeled peptide and EBP-Ig only. Peptide concentration dependent competitive reduction in mP values were determined and an $IC_{50}$ value calculated. The results are shown in Table 3.

TABLE 3

| RWJ Number | EBP Bead Binding IC50 (µM) | EBP-Ig Binding IC 50 (µLM) | FDCP-P1-hER ED50 (µM) | DPDPB cross-linking | FP/EBP-Ig IC50 (µM) |
|---|---|---|---|---|---|
| 61233 | 5 | 1 | 0.1 | positive | 0.5 |
| 61279 | 70 | 60 | 8 | positive | 6 |
| 61177 | 90 | 500 | Inactive | negative | Inactive |
| 61718 | 3 | 0.1 | 0.1 | positive | 0.35 |
| 62021 | 150 | 400 | Inactive | weakly positive | 5 |
| 61596 | 8 | | 0.08 | | |

The EPO mimetic peptides and their derivatives described here (Table 2) have been analyzed in a number of different assay systems with the intention of understanding their mode of interaction with the receptor and to establish robust methods for the discovery of ligands which bind to and activate the EPO receptor. Cell proliferation studies (Table 3) indicate which peptides have the potential to activate the EPO receptor and DPDPB crosslinking studies have defmed peptide determinants essential in the dimerization of EBP in solution (FIG. 8). Receptor-ligand competition binding studies on EBP beads have the receptor immobilized on a surface such that dimerization is physically unlikely and might be considered to monitor the ability of a given competitor to act on monomer receptor. Conversely, since each EBP-Ig molecule contains two ligand binding domains it represents a preformed template to detect ligand dependent receptor dimerization. Use of ligands as structurally distinct as radiolabeled EPO and fluorescein-RWJ 61718 in different assay formats provides diverse information with regard to the complete profile of a competitor's receptor binding properties. For example, RWJ 61233 functions as an EPO mimetic in cell proliferation studies, competes at similar levels in both the EBP-bead and EBP-Ig binding assays, was positive in the DPDPB crosslinking study and in the FP/EBP-Ig assay which uses fluorescein-RWJ 61718 as the labelled ligand. Basically, peptides with proliferative capacity such as RWJ 61279 and RWJ 61718 behave in a similar fashion in all of the assay systems.

Peptides without proliferative capacity, such as RWJ 61177, can be deficient in crosslinking ability (receptor dimerization) and provide significantly different values in the EBP bead and EBP-Ig binding assays (90 vs 500 µM) while being inactive in the FP-EBP-Ig assay. Conversely, peptides without proliferative potential but with some crosslinking potential, such as RWJ 62021, function as very efficient competitors in the FP/EBP-Ig but very poorly in the EBP-bead and EBP-Ig binding assays indicating that the behavior of the competitor is dependent upon the nature of the labelled ligand.

EBP-Ig can be used, with various ligands, to detect both productive (having proliferative capacity) and non-productive (without proliferative capacity) dimerization in the FP based assay and as such is particularly useful for the discovery and description of receptor antagonists and agonists. This suggests that other receptor-Ig fusions can be used to detect both productive and non-productive dimerization. Examples of other such receptor-Ig fusions include, but are not limited to, receptors which bind to growth factors, cytokines, neurotrophins, interleukins and interferons.

What is claimed is:

1. A method of identifying a modulator that dimerizes a receptor, comprising the steps:
   (a) combining a known concentration of a compound suspected of being a modulator and a known concentration of a receptor-dimerizing ligand which is labeled, wherein said ligand is capable of binding a preformed dimerization template, with a preformed dimerization template, wherein said preformed dimerization template comprises a ligand binding domain of an erythropoietin receptor;
   (b) measuring competitive binding of said suspected modulator and said ligand to said preformed dimerization template by quantifying the amount of bound ligand, wherein a lower amount of bound ligand in the presence compared to the absence of said suspected modulator indicates binding of said suspected modulator to said preformed dimerization template;
   (c) combining the modulator of step (b) that binds to said preformed dimerization template with cells that proliferate in response to said ligand binding to said cells; and
   (d) measuring the proliferation of said cells in the presence of said modulator,
   wherein an increase in proliferation in the presence of said modulator indicates formation of a dimerized receptor.

* * * * *

```
                         SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iv) ANTI-SENSE: NO (xi) SEQUENCE DESCRIPTION: SEQ ID NO:1:

Gly Gly Thr Tyr Ser Cys His Phe Gly Pro Leu Thr Trp Val Cys
1               5                  10                  15

Lys Pro Gln Gly Gly
                20

(2) INFORMATION FOR SEQ ID NO:2:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: peptide (iv) ANTI-SENSE: NO (xi) SEQUENCE DESCRIPTION: SEQ ID NO:2:

Tyr Ser Cys His Phe Gly Pro Leu Tyr Trp Val Cys Lys
1               5                  10

(2) INFORMATION FOR SEQ ID NO:3:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: peptide (iv) ANTI-SENSE: NO (xi) SEQUENCE DESCRIPTION: SEQ ID NO:3:

Ser Cys His Phe Gly Pro Leu Thr Trp Val Cys Lys
1               5                  10

(2) INFORMATION FOR SEQ ID NO:4:

(i) SEQUENCE CHARACTERISTICS:
          (A) LENGTH: 20 amino acids
```

(B) TYPE: amino acid
        (C) STRANDEDNESS: single
        (D) TOPOLOGY: linear (ii) MOLECULE TYPE: peptide (iv) ANTI-SENSE: NO (xi) SEQUENCE DESCRIPTION: SEQ ID NO:4:

Gly Gly Thr Tyr Ser Cys His Phe Gly Pro Leu Thr Trp Val Cys
1               5                  10                  15

Lys Pro Gln Gly Gly
            20

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iv) ANTI-SENSE: NO (xi) SEQUENCE DESCRIPTION: SEQ ID NO:5:

Gly Gly Lys Tyr Ala Cys His Met Gly Pro Met Thr Trp Val Cys
1               5                  10                  15

Gln Pro Lys Arg Gly
            20

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (iv) ANTI-SENSE: NO (xi) SEQUENCE DESCRIPTION: SEQ ID NO:6:

Gly Gly Thr Tyr Ser Cys His Phe Gly Pro Leu Thr Trp Val Cys
1               5                  10                  15

Lys Pro Gln (2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: cDNA (iv) ANTI-SENSE: NO (xi) SEQUENCE DESCRIPTION: SEQ ID NO:7:

GCATCTGCAG CGCCCCCGCC GAATCTTCCG GAC                                33

(2) INFORMATION FOR SEQ ID NO:8:

(i) SEQUENCE CHARACTERISTICS:
        (A) LENGTH: 33 base pairs

-continued

```
            (B) TYPE: nucleic acid
            (C) STRANDEDNESS: double
            (D) TOPOLOGY: linear (ii) MOLECULE TYPE: cDNA (iv) ANTI-SENSE: NO (xi) SEQUENCE DESCRIPTION: SEQ ID NO:8:

TCACTCTGCA GAGTCCAGGT CGCTAGGCGT CAG                                    33

(2) INFORMATION FOR SEQ ID NO:9:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iv) ANTI-SENSE: NO (xi) SEQUENCE DESCRIPTION: SEQ ID NO:9:

Ser Ala Glu Pro Lys Ser Cys Asp Lys
1               5

(2) INFORMATION FOR SEQ ID NO:10:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iv) ANTI-SENSE: NO (xi) SEQUENCE DESCRIPTION: SEQ ID NO:10:

Ser Ala Glu Pro Ser Ser Ser Asp Ser
1               5
```